(12) United States Patent
Alavattam et al.

(10) Patent No.: US 11,596,620 B2
(45) Date of Patent: Mar. 7, 2023

(54) FORMULATIONS WITH REDUCED OXIDATION

(71) Applicant: Genentech, Inc., South San Francisco, CA (US)

(72) Inventors: Sreedhara Alavattam, South San Francisco, CA (US); Mary Mallaney, South San Francisco, CA (US); Parbir Grewal, South San Francisco, CA (US)

(73) Assignee: F. HOFFMANN-LA ROCHE AG, Basel (CH)

( * ) Notice: Subject to any disclaimer, the term of this patent is extended or adjusted under 35 U.S.C. 154(b) by 0 days.

(21) Appl. No.: 15/821,470

(22) Filed: Nov. 22, 2017

(65) Prior Publication Data

US 2018/0318256 A1 Nov. 8, 2018

Related U.S. Application Data

(63) Continuation of application No. 15/385,788, filed on Dec. 20, 2016, now abandoned, which is a continuation of application No. 14/724,568, filed on May 28, 2015, now abandoned, which is a continuation of application No. 14/207,911, filed on Mar. 13, 2014, now abandoned.

(60) Provisional application No. 61/780,852, filed on Mar. 13, 2013.

(51) Int. Cl.
| | |
|---|---|
| *A61K 31/405* | (2006.01) |
| *A61K 39/395* | (2006.01) |
| *C07K 16/28* | (2006.01) |
| *C07K 16/24* | (2006.01) |
| *G01N 33/68* | (2006.01) |
| *C12Q 1/28* | (2006.01) |
| *A61K 39/00* | (2006.01) |

(52) U.S. Cl.
CPC ...... *A61K 31/405* (2013.01); *A61K 39/39533* (2013.01); *A61K 39/39591* (2013.01); *C07K 16/241* (2013.01); *C07K 16/2878* (2013.01); *C12Q 1/28* (2013.01); *G01N 33/6854* (2013.01); *A61K 2039/505* (2013.01); *C07K 2317/52* (2013.01); *C07K 2317/55* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,122,469 A | 6/1992 | Mather et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,648,237 A | 7/1997 | Carter |
| 5,661,016 A | 8/1997 | Lonberg et al. |
| 5,789,199 A | 8/1998 | Joly et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,248,516 B1 | 6/2001 | Winter et al. |
| 6,417,429 B1 | 7/2002 | Hein et al. |
| 6,420,548 B1 | 7/2002 | Vézina et al. |
| 6,540,791 B1 * | 4/2003 | Dias .......... A61K 8/22 8/101 |
| 6,919,436 B2 | 7/2005 | Lihme et al. |
| 6,982,321 B2 | 1/2006 | Winter |
| 7,078,492 B2 | 7/2006 | Pirofski et al. |
| 7,087,409 B2 | 8/2006 | Barbas, III et al. |

(Continued)

FOREIGN PATENT DOCUMENTS

| | | |
|---|---|---|
| CA | 2230389 A1 | 10/1999 |
| CN | 1662550 A | 8/2005 |

(Continued)

OTHER PUBLICATIONS

Haberger et al. (MAbs. Mar. 1, 2014; 6(2): 327-339) (Year: 2014).*

(Continued)

*Primary Examiner* — Sergio Coffa

(74) *Attorney, Agent, or Firm* — Morrison & Foerster LLP

(57) ABSTRACT

The invention provides formulations comprising a protein in combination with a compound that prevents oxidation of the protein. The invention also provides methods for making such formulations and methods of using such formulations. The invention further provides methods of screening for compounds that prevent oxidation of a protein in a protein composition and methods of preventing oxidation of a protein in a formulation.

16 Claims, 8 Drawing Sheets

(56) References Cited

U.S. PATENT DOCUMENTS

| | | | |
|---|---|---|---|
| 7,125,978 B1 | 10/2006 | Vézina et al. | |
| 7,153,507 B2 | 12/2006 | van de Winkel et al. | |
| 7,189,826 B2 | 3/2007 | Rodman | |
| 7,807,142 B2 | 10/2010 | Chen et al. | |
| 10,653,779 B2 * | 5/2020 | Alavattam | A61K 39/39591 |
| 2004/0116350 A1 | 6/2004 | Wentworth, Jr. et al. | |
| 2004/0213785 A1 | 10/2004 | Yamazaki et al. | |
| 2005/0026229 A1 | 2/2005 | Reiter et al. | |
| 2005/0100546 A1 | 5/2005 | Jakobovits et al. | |
| 2005/0176122 A1 | 8/2005 | Lihme et al. | |
| 2005/0260186 A1 | 11/2005 | Bookbinder et al. | |
| 2005/0276823 A1 | 12/2005 | Cini et al. | |
| 2005/0287149 A1 | 12/2005 | Keler et al. | |
| 2006/0059575 A1 | 3/2006 | Kusunoki et al. | |
| 2006/0104968 A1 | 5/2006 | Bookbinder et al. | |
| 2006/0183887 A1 | 8/2006 | Jakobovits et al. | |
| 2006/0258841 A1 | 11/2006 | Michl et al. | |
| 2008/0124326 A1 * | 5/2008 | Rehder | A61K 47/02 424/133.1 |
| 2008/0176822 A1 | 7/2008 | Chen | |
| 2010/0068210 A1 * | 3/2010 | Ji | A61K 9/0019 514/1.1 |
| 2011/0171217 A1 | 7/2011 | Badkar et al. | |
| 2012/0009276 A1 | 1/2012 | De Groote | |
| 2013/0302911 A1 * | 11/2013 | Lim | G01N 33/583 436/501 |
| 2014/0314778 A1 | 10/2014 | Alavattam et al. | |
| 2014/0322203 A1 | 10/2014 | Alavattam et al. | |
| 2016/0108125 A1 | 4/2016 | Alavattam et al. | |
| 2017/0196837 A1 | 7/2017 | Alavattam et al. | |

FOREIGN PATENT DOCUMENTS

| | | |
|---|---|---|
| CN | 1897969 A | 1/2007 |
| CN | 101074208 A | 11/2007 |
| CN | 101438158 A | 5/2009 |
| CN | 101537173 A | 9/2009 |
| EP | 0 073 657 B1 | 12/1990 |
| EP | 0 402 226 A1 | 12/1990 |
| EP | 0 183 070 B1 | 10/1991 |
| EP | 0 308 936 B1 | 7/1994 |
| EP | 0 404 097 B1 | 9/1996 |
| EP | 0 244 234 B2 | 11/2001 |
| EP | 1197221 A1 | 4/2002 |
| EP | 1 260 230 A1 | 11/2002 |
| JP | 2005-524601 A | 8/2005 |
| JP | 2007-319124 A | 12/2007 |
| JP | 2011-516483 A | 5/2011 |
| JP | 2012-502102 A | 1/2012 |
| JP | 2012500263 A | 1/2012 |
| JP | 2016-520521 A | 7/2016 |
| KR | 20150130397 A | 11/2015 |
| RU | 2134120 C1 | 8/1999 |
| RU | 2414237 C2 | 3/2010 |
| RU | 2010136488 A | 3/2012 |
| WO | WO-1987/000195 A1 | 1/1987 |
| WO | WO-1990/003430 A1 | 4/1990 |
| WO | WO-1990/013646 A1 | 11/1990 |
| WO | WO-1991/000360 A1 | 1/1991 |
| WO | WO-1991/010741 A1 | 7/1991 |
| WO | WO-1992/009690 A2 | 6/1992 |
| WO | WO-1992/020373 A1 | 11/1992 |
| WO | WO-1993/001161 A1 | 1/1993 |
| WO | WO-1993/006213 A1 | 4/1993 |
| WO | WO-1993/008829 A1 | 5/1993 |
| WO | WO-1993/016185 A2 | 8/1993 |
| WO | WO-1994/004690 A1 | 3/1994 |
| WO | WO-1994/011026 A2 | 5/1994 |
| WO | WO-1996/007754 A1 | 3/1996 |
| WO | WO-1996/027011 A1 | 9/1996 |
| WO | WO-1996/033735 A1 | 10/1996 |
| WO | WO-1996/034096 A1 | 10/1996 |
| WO | WO-1998/024893 A2 | 6/1998 |
| WO | WO-2002/22573 A2 | 3/2002 |
| WO | WO-2002/22573 A3 | 3/2002 |
| WO | 03018056 A1 | 3/2003 |
| WO | 2007095288 A2 | 8/2007 |
| WO | WO 2007/140249 * | 12/2007 |
| WO | WO-2009/145982 A1 | 12/2009 |
| WO | 2010021752 A1 | 2/2010 |
| WO | WO-2010/030670 A | 3/2010 |
| WO | WO-2010/032220 A1 | 3/2010 |
| WO | 2011163458 A2 | 12/2011 |
| WO | WO-2012/170883 A1 | 12/2012 |
| WO | 2013001044 A1 | 1/2013 |
| WO | WO-2014/160495 A1 | 10/2014 |

OTHER PUBLICATIONS

NCBI Reference Sequence NP609174.1 (downloaded on Jun. 3, 2019 from URL:< https://www.ncbi.nlm.nih.gov/protein/NP_609174.1> ) (Year: 2019).*

Stamnaes et al. (J Biol Chem. Aug. 13, 2010; 285(33): 25402-25409) (Year: 2010).*

Simat et al. (J. Agric. Food Chem.1998, 46, 2, 490-498) (Year: 1998).*

PDB (downloaded on Dec. 13, 2019 from URL:< https://www.ebi.ac.uk/pdbe/entry/pdb/2b2x/protein/2>) (Year: 2019).*

Fakih et al. (Clin Colorectal Cancer. Jul. 2006;6(2):152-6) (Year: 2006).*

Kumar et al. (Int. J. Biochem. Cell Biol. vol. 29, No. 1, pp. 129-134. 1997) (Year: 1997).*

Liu et al. (Arch Biochem Biophys. Apr. 1993;302(1):118-27, abstract only) (Year: 1993).*

Karbownik et al. (Journal of Cellular Biochemistry 81:693-699 (2001)) (Year: 2001).*

DrugBank (downloaded on Apr. 14, 2020 from URL:< https://www.drugbank.ca/drugs/DB00002>) (Year: 2020).*

Barelli, S. et al. (2008). "Oxidation of Proteins: Basic Principles and Perspectives for Blood Proteomics," *Proteomics Clin. Appl.* 2:142-157.

Belikov, V.G. et al. (1993). *Pharmaceutical Chemistry. In Two Parts, 1. General Pharmaceutical Chemistry, Second Addition, and Revised Supplemented*, Moscow, "Vyshaya shkola", pp. 43-46, (English Translation).

Herraiz, T. et al. (Mar. 2004). "Endogenous and Dietary Indoles: A Class of Antioxidants and Radical Scavengers in the ABTS Assay," *Free Radical Research* 38(3):323-331.

Loer, C.M. et al. (Dec. 1993). "Serotonin-Deficient Mutants and Male Mating Behavior in the Nematode *Caenorhabditis elegans*," *Journal of Neuroscience* 13(12):5407-5417.

Sergeev, P.V. et al. (Feb. 1976). "Effect of Tryptophan, 5-Hydroxytryptophan, Serotonin, Histidine, and Histamine on Peroxidation of Lipids in Liver Mitochondrial Membranes," *Bulletin of Experimental Biology and Medicine* 81(2):170-172.

Babu et al., "Tryptophan as an Endogenous Photosensitizer to Elicit Harmful Effects of Ultraviolet B", Indian Journal of Biochemistry and Biophysics, vol. 29, Jun. 1992, pp. 296-298.

Baltazar et al., "Antioxidant Properties and Associated Mechanisms of Salicylates", Current Medicinal Chemistry, vol. 18, Issue 21, 2011, pp. 3252-3264.

Barbas III et al., "Semisynthetic Combinatorial Antibody Libraries: A Chemical Solution to the Diversity Problem", PNAS, Proceedings of the National Academy of Sciences, vol. 89, May 1992, pp. 4457-4461.

Barbas III et al., "Assembly of Combinatorial Antibody Libraries on Phage Surfaces: The Gene III Site", Proceedings of the National Academy of Sciences, vol. 88, Sep. 1991, pp. 7978-7982.

Barnes et al., "Methods for Growth of Cultured Cells in Serum-Free Medium", Analytical Biochemistry, vol. 102, 1980, pp. 255-270.

Bass et al., "Hormone Phage: An Enrichment Method for Variant Proteins With Altered Binding Properties", Proteins: Structure, Function, and Genetics, vol. 8, 1990, pp. 309-314.

Bent et al., "Excited State Chemistry of Aromatic Amino Acids and Related Peptides. III, Tryptophan", Journal of the American Chemical Society, vol. 97, No. 10, May 14, 1975, pp. 2612-2619.

(56) References Cited

OTHER PUBLICATIONS

Bertolotti-Ciarlet et al., "Impact of Methionine Oxidation on the Binding of Human TgG1 to FcRn and Fcγ Receptors", Molecular Immunology, vol. 46, May 2009, pp. 1878-1882.
Boerner et al., "Production of Antigen-specific Human Monoclonal Antibodies from in Vitro-primed Human Splenocytes", The Journal of Immunology, vol. 147, No. 1, Jul. 1, 1991, pp. 86-95.
Brennan, Maureen, "Preparation of Bispecific Antibodies by Chemical Recombination of Monoclonal Immunoglobulin $G_1$ Fragments", Science, vol. 229, Jul. 5, 1985, pp. 81-83.
Brodeur et al., "Mouse-Human Myeloma Partners for the Production of Heterohybridomas", Monoclonal Antibody Production Techniques and Applications, Chapter 4, 1987, pp. 51-63.
Brüggemann et al., "Designer Mice: The Production of Human Antibody Repertoires in Transgenic Animals", Year Immunology, vol. 7, 1993, pp. 33-40.
Cadenas, E. et al. (1989). "Antioxidant Activity of 5-Hydroxytryptophan, 5-Hydroxyindole, and DOPA Against Microsomal Lipid Peroxidation and its Dependence on Vitamin E." *Free Radical Research Communications* 6(1):11-17.
Capelle et al., "High Throughput Screening of Protein Formulation Stability: Practical Considerations", European Journal of Pharmaceutics and Biopharmaceutics, vol. 65, 2007, pp. 131-148.
Carter et al., "High Level *Escherichia coli* Expression and Production of a Bivalent Humanized Antibody Fragment", Biotechnology, vol. 10, Feb. 1992, pp. 163-167.
Carter et al., "Humanization of an Anti-p185$^{HER2}$ Antibody for Human Cancer Therapy", Proc. Natl. Acad. Sci., vol. 89, May 1992, pp. 4285-4289.
Champe et al., "Monoclonal Antibodies That Block the Activity of Leukocyte Function-associated Antigen 1 Recognize Three Discrete Epitopes in the Inserted Domain of CDLLa", The Journal of Biological Chemistry, vol. 270, No. 3, 1995, pp. 1388-1394.
Chao et al., "Modification of Protein Surface Hydrophobicity and Methionine Oxidation by Oxidative Systems", PNAS, Proceedings of the National Academy of Sciences, vol. 94, Apr. 1997, pp. 2969-2974.
Charlton, Keith A., "Expression and Isolation of Recombinant Antibody Fragments in *E. coli*", Methods in Molecular Biology, vol. 248, 2003, pp. 245-254.
Chothia et al., "Canonical Structures for the Hypervariable Regions of Immunoglobulins", Journal of Molecular Biology, vol. 196, 1987, pp. 901-917.
Christen et al., "Antioxidant Activities of Some Tryptophan Metabolites: Possible Implication for Inflammatory Diseases", Proceedings of the National Academy of Sciences, vol. 87, Apr. 1990, pp. 2506-2510.
Clackson et al., "Making Antibody Fragments Using Phage Display Libraries", Nature, vol. 352, Aug. 15, 1991, pp. 624-628.
Cole et al., "The EBV-Hybridoma Technique and its Application to Human Lung Cancer", Monoclonal Antibodies and Cancer Therapy, 1985, pp. 77-96.
Creed, David, "The Photophysics and Photochemistry of The Near-UV Absorbing Amino Acids-I. Tryptophan and Its Simple Derivatives", Photochemistry and Photobiology, vol. 39, No. 4, 1984, pp. 537-562.
Dad et al., "Identification and Reactivity of the Triplet Excited State of 5-Hydroxytryptophan", J Photochem Photobiol B., vol. 78, No. 3, Mar. 1, 2005, pp. 245-251.
Davies, Michael J., "Singlet Oxygen-Mediated Damage to Proteins and its Consequences", Biochemical and Biophysical Research Communications, vol. 305, 2003, pp. 761-770.
Duchosal et al., "Immunization of hu-PBL—SCID Mice and The Rescue of Human Monoclonal Fab Fragments Through Combinatorial Libraries", Nature, vol. 355, Jan. 16, 1992, pp. 258-262.
Embleton et al., "In-Cell PCR From mRNA: Amplifying and Linking the Rearranged Immunoglobulin Heavy and Light Chain V-genes within Single Cells", Nucleic Acids Research, vol. 20, Issue 15, 1992, pp. 3831-3837.

Estevão, M.S. et al. (Jan. 5, 2011, e-pub. Nov. 4, 2010). "Analysis of the Antioxidant Activity of an Indole Library: Cyclic Voltammetry Versus ROS Scavenging Activity," *Tetrahedron Letters* 52(1):101-106.
Even et al., "Serum-free Hybridoma Culture: Ethical, Scientific and Safety Considerations", Trends in Biotechnology, vol. 24, Issue 3, Mar. 2006, pp. 105-108.
Fellouse et al., "Synthetic Antibodies from a Four-amino-acid Code: A Dominant Role for Tyrosine in Antigen Recognition", PNAS, vol. 101, No. 34, 2004, pp. 12467-12472.
Fishwild et al., "High-Avidity Human IgGK Monoclonal Antibodies Frotn a Novel Strain of Minilocus Transgenic Mice", Nature Biotechnology, vol. 14, Jul. 1996, pp. 845-851.
Fleer et al., "Stable Multicopy Vectors for High-Level Secretion of Recombinant Human Serum Albumin by *Kluyveromyces* Yeasts", Biotechnology, vol. 9, Oct. 1991, pp. 968-975.
Franek, Frantisek, "Oligopeptides as Tools for Improving Productivity of Hybridoma Cells Cultures", Trends in Monoclonal Antibody Research, Chapter VI, 2005, pp. 111-122.
Frokjaer et al., "Protein Drug Stability: A Formulation Challenge", Nature Reviews Drug Discovery, vol. 4, Apr. 2005, pp. 298-306.
Gerngross, Tillman U., "Advances in the Production of Human Therapeutic Proteins in Yeasts and Filamentous Fungi", Nature Biotechnology, vol. 22, No. 11, Nov. 2004, pp. 1409-1414.
Goding, James W., "Production of Monoclonal Antibodies", Monoclonal Antibodies Principles and Practice, Chapter 3 and Chapter 4, 1983, pp. 56-103.
Graham et al., "Characteristics of a Human Cell Line Transformed by DNA from Human Adenovirus Type 5", Journal of General Virology, vol. 36, 1977, pp. 59-72.
Gram et al., "In Vitro Selection and Affinity Maturation of Antibodies from a Naive Combinatorial Immunoglobulin Library", PNAS, vol. 89, Apr. 1992, pp. 3576-3580.
Grewal, P. et al. (Apr. 7, 2014). "Screening Methods to Identify Indole Derivatives That Protect against Reactive Oxygen Species Induced Tryptophan Oxidation in Proteins", *Molecular Pharmaceutics* 11(4):1259-1272.
Griffiths et al., "Human Anti-Self Antibodies with High Specificity from Phage Display Libraries", The EMBO Journal vol. 12, No. 2, 1993, pp. 725-734.
Gruber et al., "Efficient Tumor Cell Lysis Mediated by a Bispecific Single Chain Antibody Expressed in *Escherichia coli*", The Journal of Immunology, vol. 152, No. 11, 1994, pp. 5368-5374.
Gülcin, I. (Dec. 2008). "Measurement of Antioxidant ability of Melatonin and Serotonin by the DMPD and CUPRAC Methods as Trolox Equivalent," *Journal of Enzyme Inhibition And Medicinal Chemistry* 23(6):871-876.
Guss et al., "Structure of The IgG-binding Regions of Streptococcal Protein G", The EMBO Journal, vol. 5, No. 7, 1986, pp. 1567-1575.
Ham et al., "Media and Growth Requirements", Methods in Enzymology, vol. 58, 1979, pp. 44-93.
Ham, S.S. et al. (Apr. 30, 1999). "Antioxidant Effects of Serotonin and L-DOPA on Oxidative Damages of Brain Synaptosomes," *The Korean Journal of Physiology & Pharmacology* 3:147-155.
Hamers-Casterman et al., "Naturally Occurring Antibodies Devoid of Light Chains", Nature, vol. 363, Jun. 3, 1993, pp. 446-448.
Hämmerling et al., "Monoclonal Antibodies and T-Cell Hybridomas", Research Monographs in Immunology, vol. 3, 1981, 14 pages.
Harlow et al., "Antibodies: A Laboratory Manual", Cold Spring Harbor Laboratory, Chapters, titled "Immunizations", 1988, pp. 53-137.
Harris, W. J., "Production of Humanized Monoclonal Antibodies for in Vivo Imaging and Therapy", Therapeutic Monoclonals, vol. 23, 1995, pp. 1035-1038.
Hawkins et al., "Selection of Phage Antibodies by Binding Affinity: Mimicking Affinity Maturation", Journal of Molecular Biology, vol. 226, 1992, pp. 889-896.
Hawkins, C.L. et al. (Jan. 1, 2001). "Generation and Propagation of Radical Reactions on Proteins," *Biochimica et Biophysica Acta* 1504:196-219.
Hogrefe et al., "A Bacteriophage Lambda Vector for the Cloning and Expression of Immunoglobulin Fab Fragments on the Surface of Filamentous Phage", Gene, vol. 128, 1993, pp. 119-126.

(56) References Cited

OTHER PUBLICATIONS

Holliger et al., "Diabodies: Small Bivalent and Bispecific Antibody Fragments", Proceedings of the National Academy of Sciences, USA, vol. 90, Jul. 1993, pp. 6444-6448.

Hongo et al., "Development and Characterization of Murine Monoclonal Antibodies to the Latency-Associated Peptide of Transforming Growth Factor $\beta_1$", Hybridoma. vol. 14, No. 3, 1995, pp. 253-260.

Hoogenboom et al., "By-passing Immunisation: Human Antibodies from Synthetic Repertoires Of Germline $V_H$ Gene Segments Rearranged In Vitro", Journal of Molecular Biology, vol. 227, 1992, pp. 381-388.

Hoogenboom, Hennie R., "Overview of Antibody Phage-Display Technology and Its Applications", Methods in Molecular Biology, vol. 178, 2001, pp. 1-37.

Hoogenboom' et al., "Multi-Subunit Proteins on the Surface of Filamentous Phage: Methodologies for Displaying Antibody (Fab) Heavy and Light Chains", Nucleic Acids Research, vol. 19, No. 15, 1991, pp. 4133-4137.

Hudson et al., "Engineered Antibodies", Nature Medicine, vol. 9, No. 1, Jan. 2003, pp. 129-134.

Hurle et al., "Protein Engineering Techniques for Antibody Humanization", Current Opinion in Biotechnology, vol. 5, Aug. 1994, pp. 428-433.

Igarashi et al., "Photoreactivity of Amino Acids: Tryptophan-induced Photochemical Events via Reactive Oxygen Species Generation", Analytical Sciences, vol. 23, 2007, pp. 943-948.

Jakobovits et al., "Analysis of Homozygous Mutant Chimeric Mice: Deletion of The Immunoglobulin Heavy-chain Joining Region Blocks B-cell Development and Antibody Production", Proceedings of the National Academy of Sciences, vol. 90, Mar. 1993, pp. 2551-2555.

Jakobovits et al., "Germ-line Transmission and Expression of a Human-derived Yeast Artificial Chromosome", Nature, vol. 362, Mar. 18, 1993, pp. 255-258.

Ji et al., "Methionine, Tryptophan, and Histidine Oxidation in a Model Protein, PTH: Mechanisms and Stabilization", Journal of Pharmaceutical Sciences, vol. 98, No. 12, Dec. 2009, pp. 4485-4500.

Johnson et al., "The Kabat Database and a Bioinformatics Example", Methods in Molecular Biology, Antibody Engineering: Methods Protocols, vol. 248, 2004, pp. 11-25.

Jones, Andrew J. S., "Analysis of Polypeptides and Proteins", Advanced Drug Delivery Reviews, vol. 10, 1993, pp. 29-90.

Jones, Elizabeth W., "Proteinase Mutants of *Saccharomyces cerevisiae*", Genetics, vol. 85, Jan. 1977, pp. 23-33.

Jones et al., "Materials and Methods: Rapid PCR-Cloning of Full-Length Mouse Immunoglobulin Variable Regions", Biotechnology, vol. 9, Jan. 1991, pp. 88-89.

Jones et al., "Replacing the Complementarity-Determining Regions in a Human Antibody with Those from a Mouse", Nature, vol. 321, May 29, 1986, pp. 522-525.

Kohler et al., "Continuous Cultures of Fused Cells Secreting Antibody of Predefined Specificity", Nature vol. 256, Aug. 7, 1975, pp. 495-497.

Kostelny et al., "Formation of a Bispecific Antibody by the Use of Leucine Zippers", The Journal of Immunology, vol. 148, No. 5, Mar. 1, 1992, pp. 1547-1553.

Kozbor et al., "A Human Hybrid Myeloma for Production of Human Monoclonal Antibodies", The Journal of Immunology, vol. 133, No. 6, Dec. 1984, pp. 3001-3005.

Lam et al., "Antioxidants for Prevention of Methionine Oxidation in Recombinant Monoclonal Antibody HER2", Journal of Pharmaceutical Sciences, vol. 86, No. 11, Nov. 1997, pp. 1250-1255.

Lam et al., "Site-Specific Tryptophan Oxidation Induced by Autocatalytic Reaction of Polysorbate 20 in Protein Formulation", Pharmaceutical Research, vol. 28, 2011, pp. 2543-2555.

Lee et al., "Bivalent Antibody Phage Display Mimics Natural Immunoglobulin", Journal of Immunological Methods, vol. 284, 2004, pp. 119-132.

Lee et al., "High-Affinity Human Antibodies from Phage-displayed Synthetic Fab Libraries with a Single Framework Scaffold", Journal of Molecular Biology, vol. 340, 2004, pp. 1073-1093.

Leung et al., "A Method for Random Mutagenesis of a Defined DNA Segment using a Modified Polymerase Chain Reaction", Technique—A Journal of Methods In Cell And Molecular Biology, vol. 1, No. 1, Aug. 1989, pp. 11-15.

Levine et al., "Methionine Residues as Endogenous Antioxidants in Proteins", Proceedings of the National Academy of Sciences of the United States of America, vol. 93, Dec. 1996, pp. 15036-15040.

Li et al., "Chemical Instability of Protein Pharmaceuticals: Mechanisms of Oxidation and Strategies for Stabilization", Biotechnology and Bioengineering, vol. 48, 1995, pp. 490-500.

Li et al., "Optimization of Humanized IgGs in Glycoengineered *Pichia pastoris*", Nature Biotechnology, vol. 24, No. 2, Feb. 2006, pp. 210-215.

Li et al., "Small dsRNAs Induce Transcriptional Activation In Human Cells", PNAS, vol. 103, No. 46, Nov. 2006, pp. 17337-17342.

Li et al., "Human Antibodies For Immunotherapy Development Generated Via A Human B Cell Hybridoma Technology", PNAS vol. 103, No. 10, Mar. 7, 2006, pp. 3557-3562.

Lindmark et al., "Binding of Immunoglobulins to Protein A and Immunoglobulin Levels in Mammalian Sera", Journal of Immunological Methods, vol. 62, 1983, pp. 1-13.

Lonberg et al., "Antigen-Specific Human Antibodies from Mice Comprising Four Distinct Genetic Modifications", Nature, vol. 368, Apr. 28, 1994, pp. 856-859.

Lonberg et al., "Human Antibodies from Transgenic Mice", International Reviews of immunology, vol. 13, 1995, pp. 65-93.

Manning et al., "Stability of Protein Pharmaceuticals: An Update", Pharmaceutical Research, vol. 27, No. 4, Apr. 2010, pp. 544-575.

Marks et al., "By-Passing Immunization: Building High Affinity Human Antibodies by Chain Shuffling", Biotechnology, vol. 10, Jul. 1992, pp. 779-783.

Marks et al., "By-Passing Immunization: Human Antibodies from V-gene Libraries Displayed on Phage", Journal of Molecular Biology, vol. 222, 1991, pp. 581-597.

Mather et al., "Culture of Testicular Cells in Hormone-Supplemented Serum-Free Medium", Annals of the New York Academy of Sciences, Testicular Cell Culture, 1982, pp. 44-68.

Mather, Jennie P., "Establishment and Characterization of Two Distinct Mouse Testicular Epithelial Cell Lines", Biology of Reproduction, vol. 23, 1980, pp. 243-252.

Matsuda et al., "Structure and Physical Map of 64 Variable Segments in the 3' 0.8-Megabase Region of the Human Immunoglobulin Heavy-Chain Locus", Nature Genetics, vol. 3, Jan. 1993, pp. 88-94.

McCormick et al., "Characterization of A Cell-Lethal Product from the Photooxidation of Tryptophan: Hydrogen Peroxide", Science, vol. 191, Feb. 6, 1976, pp. 468-469.

McCormick et al., "Near-Ultraviolet Photooxidation of Tryptophan. Proof of Formation of Superoxide Ion", Journal of the American Chemical Society, vol. 100, No. 1, Jan. 4, 1978, pp. 312-313.

Milstein et al., "Hybrid Hybridomas and Their Use in Immunohistochemistry", Nature, vol. 305, Oct. 6, 1983, pp. 537-540.

Morimoto et al., "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW", Journal of Biochemical and Biophysical Methods, vol. 24, 1992, pp. 107-117.

Morrison et al., "Chimeric Human Antibody Molecules: Mouse Antigen-binding Domains with Human Constant Region Domains", PNAS, vol. 81, Nov. 1984, pp. 6851-6855.

Morrison, Sherie L., "Success in Specification", Nature, vol. 368, Apr. 28, 1994, pp. 812-813.

Munson et al., "Ligand: A Versatile Computerized Approach for Characterization of Ligand-binding Systems", Analytical Biochemistry, vol. 107, 1980, pp. 220-239.

Neuberger, Michael, "Generating High-Avidity Human Mabs in Mice", Nature Biotechnology, vol. 14, Jul. 1996, 1 page.

(56) References Cited

OTHER PUBLICATIONS

Ni, Jian, "Research Progress and Future Perspectives in Antibodomics and Antibodomic Drugs", International Antibodomic Drug Industry Research Institute, Xiandai Mianyixue, vol. 26, No. 4, 2006, pp. 265-268.
Orlandi et al., "Cloning Immunoglobulin Variable Domains for Expression by the Polymerase Chain Reaction", Proceedings of the National Academy of Sciences, vol. 86, May 1989, pp. 3833-3837.
Orum et al., "Efficient Method for Constructing Comprehensive Murine Fab Antibody Libraries Displayed On Phage", Nucleic Acids Research, vol. 21, No. 19, Sep. 25, 1993, pp. 4491-4498.
Orum et al., "Sequence and Proposed Secondary Structure of the *Tetrahymena therrmophila* U3-snRNA", Nucleic Acids Research, vol. 21, No. 10, 1993, pp. 2511.
Pearlman et al., "Analysis of Protein Drugs", Peptide and Protein Drug Delivery, Chapter 6, 1991, 55 pages.
Pluckthun, Andreas, "Mono- and Bivalent Antibody Fragments Produced in *Escherichia coli*: Engineering, Folding and Antigen Binding", Immunological Reviews, No. 130, 1992, pp. 151-188.
Plückthun A., "Antibodies from *Escherichia coli*", Chapter 11, The Pharmacology of Monoclonal Antibodies, 1994, pp. 269-315.
Presta, Leonard G., "Antibody Engineering", Current Opinion in Structural Biology, vol. 2, 1992, pp. 593-596.
Presta et al., "Humanization of an Antibody Directed Against IgE", The Journal of Immunology, vol. 151, No. 5, Sep. 1, 1993, pp. 2623-2632.
Prousek, Josef, "Fenton Chemistry in Biology and Medicine", Pure and Applied Chemistry, vol. 79, No. 12, 2007, pp. 2325-2338.
Reyes et al., "Expression of Human β-Interferon cDNA Under the Control of a Thymidine Kinase Promoter from Herpes Simplex Virus", Nature, vol. 297, Jun. 17, 1982, pp. 598-601.
Riechmann et al., "Reshaping Human Antibodies for Therapy", Nature, vol. 332, Mar. 24, 1988, pp. 323-327.
Sanchez, S. et al. (Dec. 1, 2008, e-pub. Dec. 29, 2008). "Tryptophan Administration in Rats Enhances Phagocytic Function and Reduces Oxidative Metabolism," Neuroendocrinology Letters 29(6):1026-1032.
Sastry et al., "Cloning of the Immunological Repertoire in *Escherichia coli* for Generation of Monoclonal Catalytic Antibodies: Construction of a Heavy Chain Variable Region-specific cDNA Library", Proceedings of the National Academy of Sciences, vol. 86, Aug. 1989, pp. 5728-5732.
Shalaby et al., "Development of Humanized Bispecific Antibodies Reactive with Cytotoxic Lymphocytes and Tumor Cells Overexpressing the HER2 Protooncogene", The Journal of Experimental Medicine, vol. 175, Jan. 1992, pp. 217-225.
Sheriff et al., "Redefining the Minimal Antigen-binding Fragment", Nature Structural and Molecular Biology, vol. 3, No. 9, Sep. 1996, pp. 733-736.
Sidhu et al., "Phage-Displayed Antibody Libraries of Synthetic Heavy Chain Complementarity Determining Regions", Journal of Molecular Biology, vol. 338, 2004, pp. 299-310.
Sims et al., "A Humanized CD18 Antibody Can Block Function Without Cell Destruction", The Journal of Immunology, vol. 151, No. 4, Aug. 15, 1993, pp. 2296-2308.
Skerra, Arne, "Bacterial Expression of Immunoglobulin Fragments", Current Opinion in Immunology, vol. 5, 1993, pp. 256-262.
Sreedhara, "Role of Surface Exposed Tryptophan as Substrate Generators for the Antibody Catalyzed Water Oxidation Pathway", Molecular Pharmaceutics, vol. 10, 2013, pp. 278-288.
Stinchcomb et al., "Isolation and Characterisation of a Yeast Chromosomal Replicator", Nature, vol. 282, Nov. 1, 1979, pp. 39-43.
Stuss, M. et al. (Jan. 1, 2010). "N-Acetylserotonin Reduces Lipopolysaccharide-Induced Lipid Peroxidation in Vitro More Effectively Than Melatonin," Neuroendocrinology Letters 31(4):489-496.
Suresh et al., "Bispecific Monoclonal Antibodies from Hybrid Hybridomas", Methods in Enzymology, vol. 121, 1986, pp. 210-228.

Tomlinson et al., "The Repertoire of Human Germline $V_H$ Sequences Reveals About Fifty Groups of $V_H$ Segments with Different Hypervariable Loops", Journal of Molecular Biology, vol. 227, 1992, pp. 776-798.
Traunecker et al., "Bispecific Single Chain Molecules (Janusins) Target Cytotoxic Lymphocytes on HIV Infected Cells", The EMBO Journal, vol. 10, No. 12, 1991, pp. 3655-3659.
Tutt et al., "Trispecific F(ab')$_3$ Derivatives that use Cooperative Signaling via the TCR/CD3 Complex and CD2 to Activate and Redirect Resting Cytotoxic T cells", The Journal of Immunology, vol. 147, No. 1, Jul. 1, 1991, pp. 60-69.
Urlaub et al., "Isolation of Chinese Hamster Cell Mutants Deficient in Dihydrofolate Reductase Activity", Proc. Natl. Acad. Sci., vol. 77, No. 7, Jul. 1980, pp. 4216-4220.
Van Den Berg et al., "*Kluyveromyces* as a Host for Heterologous Gene Expression: Expression and Secretion of Prochymosin", Bio/Technology, vol. 8, Feb. 1990, pp. 135-139.
Van Dijk et al., "Human Antibodies as Next Generation Therapeutics", Current Opinion in Chemical Biology, vol. 5, 2001, pp. 368-374.
Vaswani et al., "Humanized Antibodies as Potential Therapeutic Drugs", Annals of Allergy, Asthma and Immunology, vol. 81, Aug. 1998, pp. 105-116 and p. 119.
Verhoeyen et al., "Reshaping Human Antibodies: Grafting an Antilysozyme Activity", Science, vol. 239, 1988, pp. 1534-1536.
Vollmers et al., "Death by Stress: Natural IgM-Induced Apoptosis", Methods and Findings in Experimental and Clinical Pharmacology, vol. 27, No. 3, 2005, pp. 185-191.
Vollmers et al., "The "Early Birds": Natural IgM Antibodies and Immune Surveillance", Histology and Histopathology, vol. 20, 2005, pp. 927-937.
Wang et al., "Impact of Methionine Oxidation in Human IgG1 Fc on Serum Half-Life of Monoclonal Antibodies", Molecular Immunology, vol. 48, 2011, pp. 860-866.
Ward et al., "Binding Activities of a Repertoire of Single Immunoglobulin Variable Domains Secreted from *Escherichia coli*", Nature, vol. 341, Oct. 12, 1989, pp. 544-546.
Waterhouse et al., "Combinatorial Infection and In Vivo Recombination: A Strategy for Making Large Phage Antibody Repertoires", Nucleic Acids Research, 1993, vol. 21, No. 9, 1993, pp. 2265-2266.
Wei et al., "Identification of a Single Tryptophan Residue as Critical for Binding Activity in a Humanized Monoclonal Antibody against Respiratory Syncytial Virus", Analytical Chemistry, vol. 79, No. 7, Apr. 1, 2007, pp. 2797-2805.
Wentworth et al., "Antibodies have the Intrinsic Capacity to Destroy Antigens", PNAS, vol. 97, No. 20, Sep. 26, 2000, pp. 10930-10935.
Wentworth et al., "Antibody Catalysis of The Oxidation of Water", Science, vol. 293, Sep. 7, 2001, pp. 1806-1811.
Werber et al., "Analysis of 2,2'-Azobis (2-Amidinopropane) Dihydrochloride Degradation and Hydrolysis in Aqueous Solutions", Journal of Pharmaceutical Sciences, vol. 100, No. 8, Aug. 2011, pp. 3307-3315.
Williams et al., "Cloning and Sequencing of Human Immunoglobulin Vλ Gene Segments", European Journal of Immunology, vol. 23, 1993, pp. 1456-1461.
Winter et al., "Making Antibodies by Phage Display Technology", Annual Review of Immunology, vol. 12, 1994, pp. 433-455.
Xu et al., "Diversity in the CDR3 Region of $V_H$ Is Sufficient for Most Antibody Specificities", Immunity, vol. 13, Jul. 2000, pp. 37-45.
Yaniv, Moshe, "Enhancing Elements for Activation of Eukaryotic Promoters", Nature, vol. 297, May 6, 1982, pp. 17-18.
Yazaki et al., "Expression of Recombinant Antibodies in Mammalian Cell Lines", Methods in Molecular Biology, vol. 248, 2004, pp. 255-268.
Zapata et al., "Engineering Linear F(ab')2 Fragments for Efficient Production in *Escherichia coli* and Enhanced Antiproliferative Activity", Protein Engineering, vol. 8, No. 10, 1995, pp. 1057-1062.
Zhu et al., "Probing the Antibody-Catalyzed Water-Oxidation Pathway at Atomic Resolution", PNAS, vol. 101, No. 8, Feb. 24, 2004, pp. 2247-2252.

(56) References Cited

OTHER PUBLICATIONS

International Search Report and Written Opinion received for PCT Patent Application No. PCT/US2014/026841, dated Jul. 8, 2014, 9 pages.

International Search Report and Written Opinion dated Jul. 8, 2014, for PCT Application No. PCT/US14/026850, filed on Mar. 13, 2014, 9 pages.

Anraku, M. et al. (2004, e-pub. Aug. 2, 2004) "Stabilizing Mechanisms in Commercial Albumin Preparations: Octanoate and N-acetyl-L-tryptophanate Protect Human Serum Albumin Against Heat and Oxidative Stress," Biochimica et Biophysica Acta 1702:9-17.

Martinez, E. et al. (1983). "Liquid-Chromatographic Determination of Indole-3-acetic Acid and 5-Hydroxyindole-3-acetic Acid in Human Plasma," Clin. Chem. 29(7):1354-1357.

Munoz-Castaneda, J.R. Jr. et al. (Jan. 1, 2006). "Role of Serotonin In Cerebral Oxidative Stress In Rats," ACAT Neurobilogiae Experimentalis 66(1):1-6.

Narayanaswami, V. (Oct. 1, 1990). "Oxidative Damage to Mitochondria and Protection by Ebselen and Other Antioxidants," Biochemical Pharmacology 40(7):1623-1629.

Millian-Lano, S. et al. (2010). "Melatonin and Structurally-Related Compounds Protect Synaptosomal Membranes From Free Radical Damage," Int. J. Mol. Sci. 11:312-328.

Peng, K. et al. (Dec. 31, 2008). "Discovery of new Functions of Antibodies Catalyzing Water Oxidation," Chinese Journal of Cellular and Molecular Immunology 24(6):649-650, 653. (With English Translation).

Yang, J. et al. (Jul. 2007, e-pub. Feb. 13, 2007). "Determination of Tryptophan Oxidation of Monoclonal Antibody by Reversed Phase High Performance Liquid Chromatography," J. Chrom. A 1156:174-182.

\* cited by examiner

FORMULATIONS WITH REDUCED OXIDATION

CROSS-REFERENCE TO RELATED APPLICATIONS

This application is a continuation application of U.S. patent application Ser. No. 15/385,788, filed Dec. 20, 2016, which is a continuation of U.S. patent application Ser. No. 14/724,568, filed May 28, 2015, which is a continuation of U.S. patent application Ser. No. 14/207,911, filed Mar. 13, 2014, which claims the benefit of U.S. Provisional Application No. 61/780,852, filed Mar. 13, 2013, the contents of each of which are hereby incorporated by reference in their entirety.

FIELD OF THE INVENTION

This invention relates to formulations comprising a protein and further comprising a compound that prevents oxidation of said protein, methods for producing and using the formulations as well as methods of screening for compounds that prevent protein oxidation in protein compositions.

BACKGROUND OF THE INVENTION

Oxidative degradation of amino acid residues is a commonly observed phenomenon in protein pharmaceuticals. A number of amino acid residues are susceptible to oxidation, particularly methionine (Met), cysteine (Cys), histidine (His), tryptophan (Trp), and tyrosine (Tyr) (Li et al., *Biotechnology and Bioengineering* 48:490-500 (1995)). Oxidation is typically observed when the protein is exposed to hydrogen peroxide, light, metal ions or a combination of these during various processing steps (Li et al., *Biotechnology and Bioengineering* 48:490-500 (1995)). In particular, proteins exposed to light (Wei, et al., *Analytical Chemistry* 79(7):2797-2805 (2007)), AAPH or Fenton reagents (Ji et al., *J Pharm Sci* 98(12):4485-500 (2009)) have shown increased levels of oxidation on tryptophan residues, whereas those exposed to hydrogen peroxide have typically shown only methionine oxidation (Ji et al., *J Pharm Sci* 98(12):4485-500 (2009)). Light exposure can result in protein oxidation through the formation of reactive oxygen species (ROS) including singlet oxygen, hydrogen peroxide and superoxide (Li et al., *Biotechnology and Bioengineering* 48:490-500 (1995); Wei, et al., *Analytical Chemistry* 79(7): 2797-2805 (2007); Ji et al., *J Pharm Sci* 98(12):4485-500 (2009); Frokjaer et al., *Nat Rev Drug Discov* 4(4):298-306 (2005)), whereas protein oxidation typically occurs via hydroxyl radicals in the Fenton mediated reaction (Prousek et al., *Pure and Applied Chemistry* 79(12):2325-2338 (2007)) and via alkoxyl peroxides in the AAPH mediated reaction (Werber et al., *J Pharm Sci* 100(8):3307-15 (2011)). Oxidation of tryptophan leads to a myriad of oxidation products, including hydroxytryptophan, kynurenine, and N-formylkynurenine, and has the potential to impact safety and efficacy (Li et al., *Biotechnology and Bioengineering* 48:490-500 (1995); Ji et al., *J Pharm Sci* 98(12):4485-500 (2009); Frokjaer et al., *Nat Rev Drug Discov* 4(4):298-306 (2005)). Oxidation of a particular tryptophan residue in the heavy chain complementarity determining region (CDR) of a monoclonal antibody that correlated to loss of biological function has been reported (Wei, et al., *Analytical Chemistry* 79(7):2797-2805 (2007)). Trp oxidation mediated by a histidine coordinated metal ion has recently been reported for a Fab molecule (Lam et al., *Pharm Res* 28(10):2543-55 (2011)). Autoxidation of polysorbate 20 in the Fab formulation, leading to the generation of various peroxides, has also been invoked in the same report. Autoxidation-induced generation of these peroxides can also lead to methionine oxidation in the protein during long-term storage of the drug product since Met residues in proteins have been suggested to act as internal antioxidants (Levine et al., *Proceedings of the National Academy of Sciences of the United States of America* 93(26):15036-15040 (1996)) and are easily oxidized by peroxides. Oxidation of amino acid residues has the potential to impact the biological activity of the protein. This may be especially true for monoclonal antibodies (mAbs). Methionine oxidation at Met254 and Met430 in an IgG1 mAb potentially impacts serum half-life in transgenic mice (Wang et al., *Molecular Immunology* 48(6-7):860-866 (2011)) and also impacts binding of human IgG1 to FcRn and Fc-gamma receptors (Bertolotti-Ciarlet et al., *Molecular Immunology* 46(8-9)1878-82 (2009)).

The stability of proteins, especially in liquid state, needs to be evaluated during drug product manufacturing and storage. The development of pharmaceutical formulations sometimes includes addition of antioxidants to prevent oxidation of the active ingredient. Addition of L-methionine to formulations has resulted in reduction of methionine residue oxidation in proteins and peptides (Ji et al., *J Pharm Sci* 98(12):4485-500 (2009); Lam et al., *Journal of Pharmaceutical Sciences* 86(11):1250-1255 (1997)) Likewise, addition of L-tryptophan has been shown to reduce oxidation of tryptophan residues (Ji et al., *J Pharm Sci* 98(12):4485-500 (2009); Lam et al., *Pharm Res* 28(10):2543-55 (2011)). L-Trp, however, possesses strong absorbance in the UV region (260-290 nm) making it a primary target during photo-oxidation (Creed, D., *Photochemistry and Photobiology* 39(4):537-562 (1984)). Trp has been hypothesized as an endogenous photosensitizer enhancing the oxygen dependent photo-oxidation of tyrosine (Babu et al., *Indian J Biochem Biophys* 29(3):296-8 (1992)) and other amino acids (Bent et al., *Journal of the American Chemical Society* 97(10):2612-2619 (1975)). It has been demonstrated that L-Trp can generate hydrogen peroxide when exposed to light and that L-Trp under UV light produces hydrogen peroxide via the superoxide anion (McCormick et al., *Science* 191(4226):468-9 (1976); Wentworth et al., *Science* 293(5536):1806-11 (2001); McCormick et al., *Journal of the American Chemical Society* 100:312-313 (1978)). Additionally, tryptophan is known to produce singlet oxygen upon exposure to light (Davies, M. J., *Biochem Biophys Res Commun* 305(3):761-70 (2003)). Similar to the protein oxidation induced by autoxidation of polysorbate 20, it is possible that protein oxidation can occur upon ROS generation by other excipients in the protein formulation (e.g. L-Trp) under normal handling conditions.

It is apparent from recent studies that the addition of standard excipients, such as L-Trp and polysorbates, to protein compositions that are meant to stabilize the protein can result in unexpected and undesired consequences such as ROS-induced oxidation of the protein. Therefore, there remains a need for the identification of alternative excipients for use in protein compositions and the development of such compositions.

BRIEF SUMMARY OF THE INVENTION

Provided herein are formulations comprising a protein and a compound that prevents oxidation of the protein in the formulation, methods of making the formulations, and methods of screening compounds that prevent oxidation of a protein in a protein formulation.

In one aspect, provided herein is a formulation comprising a protein and a compound which prevents oxidation of the protein in the formulation, wherein the compound is of formula:

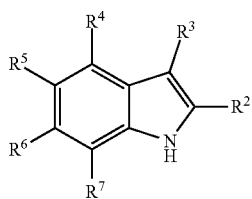

wherein $R^2$ is selected from hydrogen, hydroxyl, —COOH, and —CH$_2$COOH;

$R^3$ is selected from hydrogen, hydroxyl, —COOH, —CH$_2$COOH, and —CH$_2$CHR$^{3a}$(NH$_2$); wherein $R^{3a}$ is COOH or hydrogen;

$R^4$, $R^5$, $R^6$, and $R^7$ are independently selected from hydrogen and hydroxyl;

provided that one of $R^2$, $R^3$, $R^4$, $R^5$, $R^6$, and $R^7$ is hydroxyl;

or a pharmaceutically acceptable salt thereof.

In some embodiments, the compound is a compound of formula:

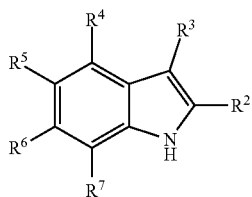

wherein $R^2$ and $R^3$ are independently selected from hydrogen, hydroxyl, —COOH, and —CH$_2$COOH; and $R^4$, $R^5$, $R^6$, and $R^7$ are independently selected from hydrogen and hydroxyl;

provided that one of $R^2$, $R^3$, $R^4$, $R^5$, $R^6$, and $R^7$ is hydroxyl;

or a pharmaceutically acceptable salt thereof.

In some embodiments, the compound is a compound of formula:

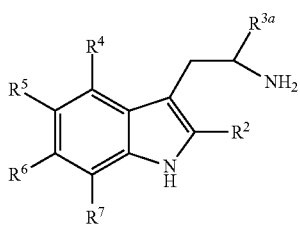

wherein $R^{3a}$ is COOH or hydrogen;

$R^2$, $R^4$, $R^5$, $R^6$, and $R^7$ are independently selected from hydrogen and hydroxyl, provided that one of $R^2$, $R^4$, $R^5$, $R^6$, and $R^7$ is hydroxyl;

or a pharmaceutically acceptable salt thereof.

In some embodiments, $R^4$, $R^5$ or $R^7$ in any of the formula above is hydroxyl. In some embodiments, the compound is selected from the group consisting of 5-hydroxy-tryptophan, 5-hydroxy indole, 7-hydroxy indole, and serotonin.

In some embodiments, the formulation is a liquid formulation. In some embodiments, the formulation is a pharmaceutical formulation suitable for administration to a subject. In some embodiments, the formulation is aqueous.

In some embodiments, the compound in the formulation is from about 0.3 mM to about 1 mM. In some embodiments, the compound prevents oxidation of tryptophan, cysteine, histidine, tyrosine, and/or methionine in the protein. In some embodiments, the compound prevents oxidation of the protein by a reactive oxygen species. In some embodiments, the reactive oxygen species is selected from the group consisting of singlet oxygen, hydrogen peroxide, a hydroxyl radical, and an alkyl peroxide.

In some embodiments, the protein is susceptible to oxidation. In some embodiments, a tryptophan amino acid in the protein is susceptible to oxidation. In some embodiments, the protein is an antibody (e.g., a polyclonal antibody, a monoclonal antibody, a humanized antibody, a human antibody, a chimeric antibody, or antibody fragment). In some embodiments, the protein concentration in the formulation is about 1 mg/mL to about 250 mg/mL.

In some embodiments, the formulation further comprises one or more excipients selected from the group consisting of a stabilizer, a buffer, a surfactant, and a tonicity agent. In some embodiments, the formulation has a pH of about 4.5 to about 7.0.

In another aspect, provided herein is a method of making a protein formulation (such as a liquid formulation) comprising adding an amount of a compound that prevents oxidation of a protein to the formulation, wherein the compound is of formula:

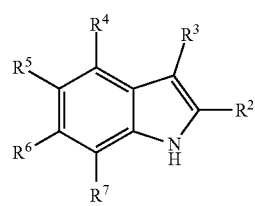

wherein $R^2$ is selected from hydrogen, hydroxyl, —COOH, and —CH$_2$COOH;

$R^3$ is selected from hydrogen, hydroxyl, —COOH, —CH$_2$COOH, and —CH$_2$CHR$^{3a}$(NH$_2$); wherein $R^{3a}$ is COOH or hydrogen;

$R^4$, $R^5$, $R^6$, and $R^7$ are independently selected from hydrogen and hydroxyl;

provided that one of $R^2$, $R^3$, $R^4$, $R^5$, $R^6$, and $R^7$ is hydroxyl;

or a pharmaceutically acceptable salt thereof.

In another aspect, provided herein is a method of preventing oxidation of a protein in a protein formulation (such as a liquid formulation) comprising adding an amount of a compound that prevents oxidation of a protein to the formulation, wherein the compound is of formula:

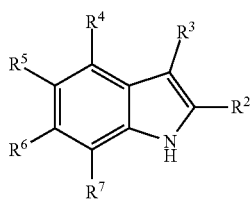

wherein $R^2$ is selected from hydrogen, hydroxyl, —COOH, and —CH$_2$COOH;

$R^3$ is selected from hydrogen, hydroxyl, —COOH, —CH$_2$COOH, and —CH$_2$CHR$^{3a}$(NH$_2$); wherein $R^{3a}$ is COOH or hydrogen;

$R^4$, $R^5$, $R^6$, and $R^7$ are independently selected from hydrogen and hydroxyl;

provided that one of $R^2$, $R^3$, $R^4$, $R^5$, $R^6$, and $R^7$ is hydroxyl;

or a pharmaceutically acceptable salt thereof.

In some embodiments of the methods described herein, the compound is a compound of formula:

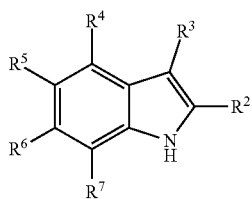

wherein $R^2$ and $R^3$ are independently selected from hydrogen, hydroxyl, —COOH, and —CH$_2$COOH; and $R^4$, $R^5$, $R^6$, and $R^7$ are independently selected from hydrogen and hydroxyl;

provided that one of $R^2$, $R^3$, $R^4$, $R^5$, $R^6$, and $R^7$ is hydroxyl;

or a pharmaceutically acceptable salt thereof.

In some embodiments of the methods described herein, the compound is a compound of formula:

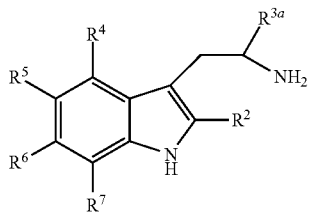

wherein $R^{3a}$ is COOH or hydrogen;

$R^2$, $R^4$, $R^5$, $R^6$, and $R^7$ are independently selected from hydrogen and hydroxyl, provided that one of $R^2$, $R^4$, $R^5$, $R^6$, and $R^7$ is hydroxyl;

or a pharmaceutically acceptable salt thereof.

In some embodiments, $R^4$, $R^5$ or $R^7$ in any of the formula above is hydroxyl. In some embodiments, the compound is selected from the group consisting of 5-hydroxy-tryptophan, 5-hydroxy indole, 7-hydroxy indole, and serotonin.

In some embodiments, the formulation is a liquid formulation. In some embodiments, the formulation is a pharmaceutical formulation suitable for administration to a subject. In some embodiments, the formulation is aqueous. In some embodiments, the compound in the formulation is from about 0.3 mM to about 1 mM.

In some embodiments, the compound prevents oxidation of tryptophan, cysteine, histidine, tyrosine, and/or methionine in the protein. In some embodiments, the compound prevents oxidation of the protein by a reactive oxygen species. In some embodiments, the reactive oxygen species is selected from the group consisting of singlet oxygen, hydrogen peroxide, a hydroxyl radical, and an alkyl peroxide.

In some embodiments, the protein is susceptible to oxidation. In some embodiments, a tryptophan amino acid in the protein is susceptible to oxidation. In some embodiments, the protein is an antibody (e.g., a polyclonal antibody, a monoclonal antibody, a humanized antibody, a human antibody, a chimeric antibody, or antibody fragment). In some embodiments, the protein concentration in the formulation is about 1 mg/mL to about 250 mg/mL.

In some embodiments, the formulation further comprises one or more excipients selected from the group consisting of a stabilizer, a buffer, a surfactant, and a tonicity agent. In some embodiments, the formulation has a pH of about 4.5 to about 7.0.

In another aspect, provided herein is a method of screening a compound that prevents oxidation of a protein in a protein composition, comprising selecting a compound that has lower oxidation potential and less photosensitivity as compared to L-tryptophan, and testing the effect of the selected compound on preventing oxidation of the protein.

In some embodiments, the photosensitivity is measured based on the amount of H$_2$O$_2$ produced by the compound upon light exposure. In some embodiments, the compound that produces less than about 10% of the amount of H$_2$O$_2$ produced by L-tryptophan is selected. In some embodiments, the oxidation potential is measured by cyclic voltammetry. In some embodiments, the selected compound is tested for the effect on preventing oxidation of the protein by reactive oxygen species generated by 2,2'-azobis(2-amidinopropane) dihydrochloride (AAPH), light, and/or a Fenton reagent.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION

I. Definitions

Figure 1:
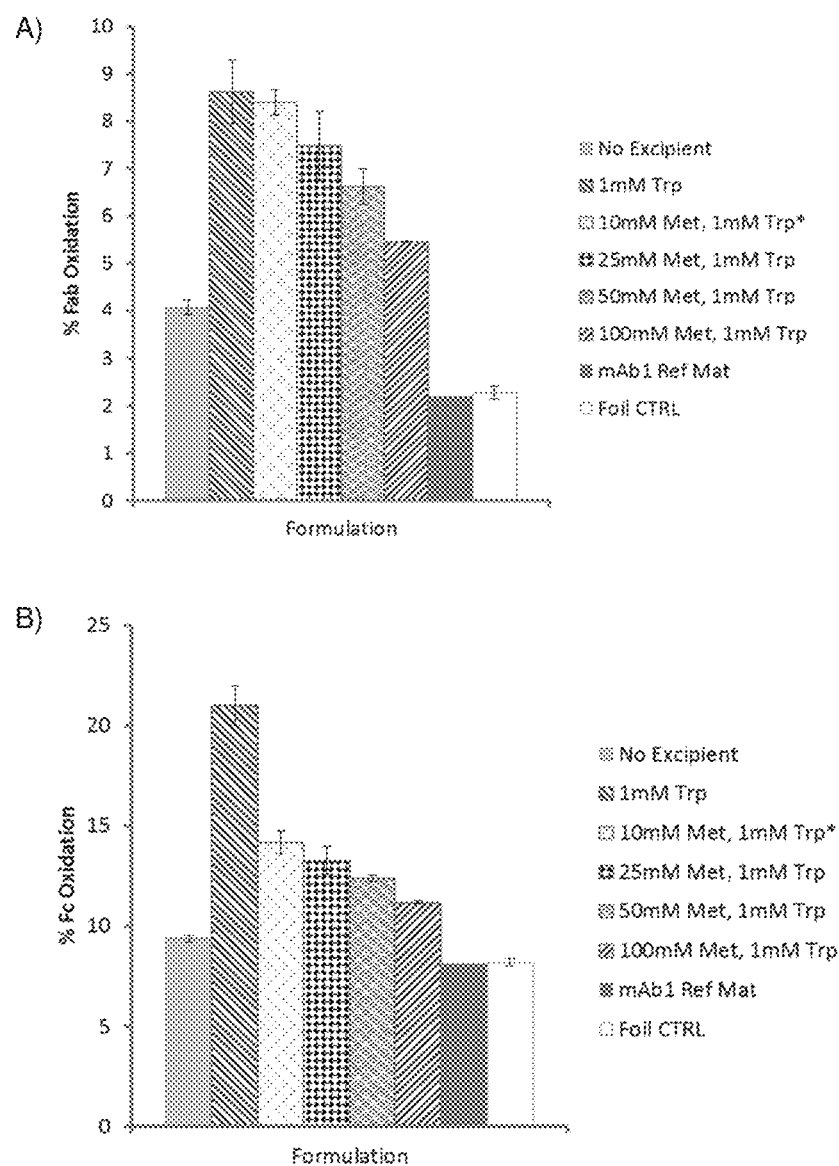
FIG. 1 is a series of graphs demonstrating the oxidation of A) Fab in mAb1, and B) Fc in mAb1 after eight hours of light exposure at 250 W/m$^2$. mAb1 was present at 5 mg/mL in 20 mM histidine acetate, 250 mM trehalose, 0.02% polysorbate 20. All vials were placed in the lightbox except the mAb1 Ref Mat. Foil CTRL vials were covered in foil before placement in the lightbox. Three separate experimental vials were averaged for each sample, except "10 mM Met, 1 mM Trp" (*) was the average of two experimental vials, and mAb1 Ref Mat was one experimental vial with three independent injections on the HPLC. Error bars represent one standard deviation.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile.

A "sterile" formulation is aseptic or free or essentially free from all living microorganisms and their spores.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in *Peptide and Protein Drug Delivery*, 247-301, Vincent Lee Ed., Marcel Dekker, Inc., New York, N.Y., Pubs. (1991) and Jones, A. *Adv. Drug Delivery Rev.* 10: 29-90 (1993), for example. Stability can be measured at a selected amount of light exposure and/or temperature for a selected time period. Stability can be evaluated qualitatively and/or quantitatively in a variety of different ways, including evaluation of aggregate formation (for example using size exclusion chromatography, by measuring turbidity, and/or by visual inspection); evaluation of ROS formation (for example by using a light stress assay or a 2,2'-Azobis(2-Amidinopropane) Dihydrochloride (AAPH) stress assay); oxidation of specific amino acid residues of the protein (for example a Trp residue and/or a Met residue of a monoclonal antibody); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or target binding function of the protein (e.g., antigen binding function of an antibody); etc. Instability may involve any one or more of: aggregation, deamidation (e.g. Asn deamidation), oxidation (e.g. Met oxidation and/or Trp oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation differences, etc.

A protein "retains its physical stability" in a pharmaceutical formulation if it shows no signs or very little of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve protein oxidation which can be evaluated using tryptic peptide mapping, reverse-phase high-performance liquid chromatography (HPLC) and liquid chromatography-mass spectrometry (LC/MS), for example. Other types of chemical alteration include charge alteration of the protein which can be evaluated by ion-exchange chromatography or icIEF, for example.

A protein "retains its biological activity" in a pharmaceutical formulation, if the biological activity of the protein at a given time is within about 10% (within the errors of the assay) of the biological activity exhibited at the time the pharmaceutical formulation was prepared as determined for example in an antigen binding assay for a monoclonal antibody.

As used herein, "biological activity" of a protein refers to the ability of the protein to bind its target, for example the ability of a monoclonal antibody to bind to an antigen. It can further include a biological response which can be measured in vitro or in vivo. Such activity may be antagonistic or agonistic.

A protein which is "susceptible to oxidation" is one comprising one or more residue(s) that has been found to be prone to oxidation such as, but not limited to, methionine (Met), cysteine (Cys), histidine (His), tryptophan (Trp), and tyrosine (Tyr). For example, a tryptophan amino acid in the Fab portion of a monoclonal antibody or a methionine amino acid in the Fc portion of a monoclonal antibody may be susceptible to oxidation.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention preferably has a pH in the range from about 4.5 to about 8.0. For example, histidine acetate is an example of a buffer that will control the pH in this range.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. In one embodiment, the preservative herein is benzyl alcohol.

As used herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc.); etc. In one embodiment, the surfactant herein is polysorbate 20.

"Pharmaceutically acceptable" excipients or carriers as used herein include pharmaceutically acceptable carriers, stabilizers, buffers, acids, bases, sugars, preservatives, surfactants, tonicity agents, and the like, which are well known in the art (Remington: The Science and Practice of Pharmacy, $22^{nd}$ Ed., Pharmaceutical Press, 2012). Examples of pharmaceutically acceptable excipients include buffers such as phosphate, citrate, acetate, and other organic acids; antioxidants including ascorbic acid, L-tryptophan and methionine; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; metal complexes such as Zn-protein complexes; chelating agents such as EDTA; sugar alcohols such as mannitol or sorbitol; salt-forming counterions such as sodium; and/or nonionic surfactants such as polysorbate, poloxamer, polyethylene glycol (PEG), and PLURONICS™. "Pharmaceutically acceptable" excipients or carriers are those which can reasonably be administered to a subject to provide an effective dose of the active ingredient employed and that are nontoxic to the subject being exposed thereto at the dosages and concentrations employed.

The protein which is formulated is preferably essentially pure and desirably essentially homogeneous (e.g., free from contaminating proteins etc.). "Essentially pure" protein means a composition comprising at least about 90% by weight of the protein (e.g., monoclonal antibody), based on total weight of the composition, preferably at least about 95% by weight. "Essentially homogeneous" protein means a composition comprising at least about 99% by weight of the protein (e.g., monoclonal antibody), based on total weight of the composition.

The terms "protein" "polypeptide" and "peptide" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, proteins containing one or more analogs of an amino acid (including, for example, unnatural amino acids, etc.), as well as other modifications known in the art. Examples of proteins encompassed within the definition herein include mammalian proteins, such as, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; leptin; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; a tumor necrosis factor receptor such as death receptor 5 and CD120; TNF-related apoptosis-inducing ligand (TRAIL); B-cell maturation antigen (BCMA); B-lymphocyte stimulator (BLyS); a proliferation-inducing ligand (APRIL); enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; platelet-derived endothelial cell growth factor (PD-ECGF); a vascular endothelial growth factor family protein (e.g., VEGF-A, VEGF-B, VEGF-C, VEGF-D, and P1GF); a platelet-derived growth factor (PDGF) family protein (e.g., PDGF-A, PDGF-B, PDGF-C, PDGF-D, and dimers thereof); fibroblast growth factor (FGF) family such as aFGF, bFGF, FGF4, and FGF9; epidermal growth factor (EGF); receptors for hormones or growth factors such as a VEGF receptor(s) (e.g., VEGFR1, VEGFR2, and VEGFR3), epidermal growth factor (EGF) receptor(s) (e.g., ErbB1, ErbB2, ErbB3, and ErbB4 receptor), platelet-derived growth factor (PDGF) receptor(s) (e.g., PDGFR-α and PDGFR-β), and fibroblast growth factor receptor(s); TIE ligands (Angiopoietins, ANGPT1, ANGPT2); Angiopoietin receptor such as TIE1 and TIE2; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-b; transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins (IGFBPs); CD proteins such as CD3, CD4, CD8, CD19 and CD20; erythropoietin; osteoinductive factors; immunotoxins; a bone morphogenetic protein (BMP); a chemokine such as CXCL12 and CXCR4; an interferon such as interferon-alpha, -beta, and -gamma; colony stimulating factors (CSFs), e.g., M-CSF, GM-CSF, and G-CSF; a cytokine such as interleukins (ILs), e.g., IL-1 to IL-10; midkine; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; ephrins; Bv8; Delta-like ligand 4 (DLL4); Del-1; BMP9; BMP10; Follistatin; Hepatocyte growth factor (HGF)/scatter factor (SF); Alk1; Robo4; ESM1; Perlecan; EGF-like domain, multiple 7 (EGFL7); CTGF and members of its family; thrombospondins such as thrombospondin1 and thrombospondin2; collagens such as collagen IV and collagen XVIII; neuropilins such as NRP1 and NRP2; Pleiotrophin (PTN); Progranulin; Proliferin; Notch proteins such as Notch1 and Notch4; semaphorins such as Sema3A, Sema3C, and Sema3F; a tumor associated antigen such as CA125 (ovarian cancer antigen); immunoadhesins; and fragments and/or variants of any of the above-listed proteins as well as antibodies, including antibody fragments, binding to one or more protein, including, for example, any of the above-listed proteins.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" protein (e.g., an isolated antibody) is one which has been identified and separated and/or recovered from a component of its natural environment. Contaminant components of its natural environment are materials which would interfere with research, diagnostic or therapeutic uses for the protein, and may include enzymes, hormones, and other proteinaceous or nonproteinaceous solutes. Isolated protein includes the protein in situ within recombinant cells since at least one component of the protein's natural environment will not be present. Ordinarily, however, isolated protein will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("lc") and lambda ("k"), based on the amino acid sequences of their constant domains.

The term IgG "isotype" or "subclass" as used herein is meant any of the subclasses of immunoglobulins defined by the chemical and antigenic characteristics of their constant regions. Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. *Cellular and Mol. Immunology*, 4th ed., W.B. Saunders, Co., 2000. An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies;

single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., Springer-Verlag, New York, pp. 269-315, 1994.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by a variety of techniques, including, for example, the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); *Neuberger, Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence The Kabat numbering system is generally used when referring to a residue in the variable domain (approximately residues 1-107 of the light chain and residues 1-113 of the heavy chain) (e.g., Kabat et al., *Sequences of Immunological*

*Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 *Protein Eng*, 8(10):1057-1062). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

The term "about" as used herein refers to an acceptable error range for the respective value as determined by one of ordinary skill in the art, which will depend in part how the value is measured or determined, i.e., the limitations of the measurement system. For example, "about" can mean within 1 or more than 1 standard deviations, per the practice in the art. A reference to "about" a value or parameter herein includes and describes embodiments that are directed to that value or parameter per se. For example, a description referring to "about X" includes description of "X".

As used in this specification and the appended claims, the singular forms "a", "an" and "the" include plural referents unless the content clearly dictates otherwise. Thus, for example, reference to "a compound" optionally includes a combination of two or more such compounds, and the like.

It is understood that aspects and embodiments of the invention described herein include "comprising," "consisting," and "consisting essentially of" aspects and embodiments.

II. Protein Formulations and Preparation

The invention herein relates to formulations comprising a protein and a compound which prevents oxidation of the protein in the formulation, the compound is of formula:

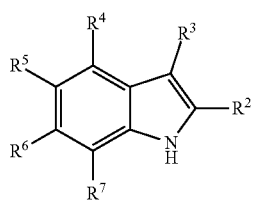

wherein $R^2$ is selected from hydrogen, hydroxyl, —COOH, and —CH$_2$COOH;

$R^3$ is selected from hydrogen, hydroxyl, —COOH, —CH$_2$COOH, and —CH$_2$CHR$^{3a}$(NH$_2$); wherein R$^{3a}$ is COOH or hydrogen; $R^4$, $R^5$, $R^6$, and $R^7$ are independently selected from hydrogen and hydroxyl; provided that one of $R^2$, $R^3$, $R^4$, $R^5$, $R^6$, and $R^7$ is hydroxyl; or a pharmaceutically acceptable salt thereof.

In some embodiments, the compound is a compound of formula:

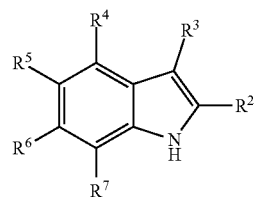

wherein $R^2$ and $R^3$ are independently selected from hydrogen, hydroxyl, —COOH, and —CH$_2$COOH; and $R^4$, $R^5$, $R^6$, and $R^7$ are independently selected from hydrogen and hydroxyl; provided that one of $R^2$, $R^3$, $R^4$, $R^5$, $R^6$, and $R^7$ is hydroxyl; or a pharmaceutically acceptable salt thereof.

In some embodiments, the compound is a compound of formula:

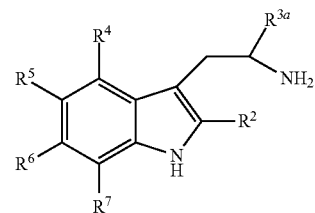

wherein R$^{3a}$ is COOH or hydrogen; $R^2$, $R^4$, $R^5$, $R^6$, and $R^7$ are independently selected from hydrogen and hydroxyl, provided that one of $R^2$, $R^4$, $R^5$, $R^6$, and $R^7$ is hydroxyl; or a pharmaceutically acceptable salt thereof.

In some embodiments, $R^4$, $R^5$ or $R^7$ in any of the formula above is hydroxyl. In a further embodiment, the compound is selected from the group consisting of 5-hydroxy-tryptophan, 5-hydroxy indole, 7-hydroxy indole, and serotonin. In some embodiments, the formulation is a liquid formulation. In some embodiments, the compound in the formulation is from about 0.3 mM to about 10 mM, or up to the highest concentration that the compound is soluble in the formulation. In some embodiments, the compound in the formulation is about 0.3 mM to about 1 mM. In some embodiments, the compound prevents oxidation of one or more amino acids in the protein selected from group consisting of tryptophan, cysteine, histidine, tyrosine, and/or methionine. In some embodiments, the compound prevents oxidation of the protein by a reactive oxygen species (ROS). In a further embodiment, the reactive oxygen species is selected from the group consisting of a singlet oxygen, a superoxide (O$_2$—), an alkoxyl radical, a peroxyl radical, a hydrogen peroxide (H$_2$O$_2$), a dihydrogen trioxide (H$_2$O$_3$), a hydrotrioxy radical (HO$_3$.), ozone (O$_3$), a hydroxyl radical, and an alkyl peroxide. In some embodiments, a protein described herein is susceptible to oxidation. In some embodiments, methionine, cysteine, histidine, tryptophan, and/or tyrosine in the protein is susceptible to oxidation. In some embodiments, tryptophan and/or methionine in the protein is susceptible to oxidation. For example, a tryptophan amino acid in the Fab portion of a monoclonal antibody and/or a methionine amino acid in the Fc portion of a monoclonal antibody can be susceptible to oxidation. In some embodiments, the protein is a therapeutic protein. In some of the embodiments herein, the protein is an antibody. In some embodiments, the antibody is a polyclonal antibody, a monoclonal antibody, a humanized antibody, a human antibody, a chimeric antibody, or an antibody fragment. In a further embodiment, the compound prevents oxidation of one or more amino acids in the Fab portion of an antibody. In another further embodiment, the compound prevents oxidation of one or more amino acids in the Fc portion of an antibody. In some embodiments, the formulation provided herein is a pharmaceutical formulation suitable for administration to a subject. As used herein a "subject" or an "individual" for purposes of treatment or administration refers to any animal classified as a mammal, including humans, domestic and farm animals, and zoo, sports, or pet animals, such as dogs, horses, cats, cows, etc. Preferably, the mammal is human. In some embodiments, the formulation is aqueous. In some embodiments herein, the protein (e.g., the antibody) concentration in the formulation is about 1 mg/mL to about 250 mg/mL. In some embodiments, the formulation further one or more excipients selected from the group consisting of a stabilizer, a buffer, a surfactant, and a tonicity agent. For example, a formulation of the invention can comprise a monoclonal antibody, a compound as provided herein which prevents oxidation of the protein (e.g., 5-hydroxy indole), and a buffer that maintains the pH of the formulation to a desirable level. In some embodiments, a formulation provided herein has a pH of about 4.5 to about 7.0.

Proteins and antibodies in the formulation may be prepared using methods known in the art. The antibody (e.g., full length antibodies, antibody fragments and multispecific antibodies) in the formulation is prepared using techniques available in the art, non-limiting exemplary methods of which are described in more detail in the following sections. The methods herein can be adapted by one of skill in the art for the preparation of formulations comprising other proteins such as peptide-based inhibitors. See *Molecular Cloning: A Laboratory Manual* (Sambrook et al., 4$^{th}$ ed., Cold Spring Harbor Laboratory Press, Cold Spring Harbor, N.Y., 2012); *Current Protocols in Molecular Biology* (F. M. Ausubel, et al. eds., 2003); *Short Protocols in Molecular Biology* (Ausubel et al., eds., J. Wiley and Sons, 2002); *Current Protocols in Protein Science*, (Horswill et al., 2006); *Antibodies, A Laboratory Manual* (Harlow and Lane, eds., 1988); *Culture of Animal Cells: A Manual of Basic Technique and Specialized Applications* (R. I. Freshney, 6$^{th}$ ed., J. Wiley and Sons, 2010) for generally well understood and commonly employed techniques and procedures for the production of therapeutic proteins, which are all incorporated herein by reference in their entirety.

A. Antibody Preparation

The antibody in the formulations provided herein is directed against an antigen of interest. Preferably, the antigen is a biologically important polypeptide and administration of the antibody to a mammal suffering from a disorder can result in a therapeutic benefit in that mammal. However, antibodies directed against nonpolypeptide antigens are also contemplated.

Where the antigen is a polypeptide, it may be a transmembrane molecule (e.g. receptor) or ligand such as a growth factor. Exemplary antigens include molecules such as vascular endothelial growth factor (VEGF); CD20; ox-LDL; ox-ApoB100; renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; a tumor necrosis factor receptor such as death receptor 5 and CD120; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des (1-3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrns such as CD11a, CD11b, CD11c, CD18, an ICAM, VLA-4 and VCAM; a tumor associated antigen such as HER2, HER3 or HER4 receptor; and fragments of any of the above-listed polypeptides.

(i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl$_2$, or R$^1$N=C=NR, where R and R$^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ⅒ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of interest can be made using the hybridoma method first described by Kohler et al., *Nature*, 256:495 (1975), and further described, e.g., in Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue*, 26(4):265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005).

For various other hybridoma techniques, see, e.g., US 2006/258841; US 2006/183887 (fully human antibodies), US 2006/059575; US 2005/287149; US 2005/100546; US 2005/026229; and U.S. Pat. Nos. 7,078,492 and 7,153,507. An exemplary protocol for producing monoclonal antibodies using the hybridoma method is described as follows. In one embodiment, a mouse or other appropriate host animal, such as a hamster, is immunized to elicit lymphocytes that produce or are capable of producing antibodies that will specifically bind to the protein used for immunization. Antibodies are raised in animals by multiple subcutaneous (sc) or intraperitoneal (ip) injections of a polypeptide of interest or a fragment thereof, and an adjuvant, such as monophosphoryl lipid A (MPL)/trehalose dicrynomycolate (TDM) (Ribi Immunochem. Research, Inc., Hamilton, Mont.). A polypeptide of interest (e.g., antigen) or a fragment thereof may be prepared using methods well known in the art, such as recombinant methods, some of which are further described herein. Serum from immunized animals is assayed for anti-antigen antibodies, and booster immunizations are optionally administered. Lymphocytes from animals producing anti-antigen antibodies are isolated. Alternatively, lymphocytes may be immunized in vitro.

Lymphocytes are then fused with myeloma cells using a suitable fusing agent, such as polyethylene glycol, to form a hybridoma cell. See, e.g., Goding, *Monoclonal Antibodies: Principles and Practice*, pp. 59-103 (Academic Press, 1986). Myeloma cells may be used that fuse efficiently, support stable high-level production of antibody by the selected antibody-producing cells, and are sensitive to a medium such as HAT medium. Exemplary myeloma cells include, but are not limited to, murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

The hybridoma cells thus prepared are seeded and grown in a suitable culture medium, e.g., a medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells. Preferably, serum-free hybridoma cell culture methods are used to reduce use of animal-derived serum such as fetal bovine serum, as described, for example, in Even et al., *Trends in Biotechnology*, 24(3), 105-108 (2006).

Oligopeptides as tools for improving productivity of hybridoma cell cultures are described in Franek, *Trends in Monoclonal Antibody Research*, 111-122 (2005). Specifically, standard culture media are enriched with certain amino acids (alanine, serine, asparagine, proline), or with protein hydrolyzate fractions, and apoptosis may be significantly suppressed by synthetic oligopeptides, constituted of three to six amino acid residues. The peptides are present at millimolar or higher concentrations.

Culture medium in which hybridoma cells are growing may be assayed for production of monoclonal antibodies that bind to an antibody described herein. The binding specificity of monoclonal antibodies produced by hybridoma cells may be determined by immunoprecipitation or by an in vitro binding assay, such as radioimmunoassay (RIA) or enzyme-linked immunoadsorbent assay (ELISA). The binding affinity of the monoclonal antibody can be determined, for example, by Scatchard analysis. See, e.g., Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods. See, e.g., Goding, supra. Suitable culture media for this purpose include, for example, D-MEM or RPMI-1640 medium. In addition, hybridoma cells may be grown in vivo as ascites tumors in an animal. Monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography. One procedure for isolation of proteins from hybridoma cells is described in US 2005/176122 and U.S. Pat. No. 6,919,436. The method includes using minimal salts, such as lyotropic salts, in the binding process and preferably also using small amounts of organic solvents in the elution process.

(iii) Certain Library Screening Methods

Antibodies described herein can be made by using combinatorial libraries to screen for antibodies with the desired activity or activities. For example, a variety of methods are known in the art for generating phage display libraries and screening such libraries for antibodies possessing the desired binding characteristics. Such methods are described generally in Hoogenboom et al. in *Methods in Molecular Biology* 178:1-37 (O'Brien et al., ed., Human Press, Totowa, N.J., 2001). For example, one method of generating antibodies of interest is through the use of a phage antibody library as described in Lee et al., *J. Mol. Biol.* (2004), 340(5):1073-93.

In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the antibodies can be obtained by designing a suitable antigen screening procedure to select for the phage clone of interest followed by construction of a full length antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

In certain embodiments, the antigen-binding domain of an antibody is formed from two variable (V) regions of about 110 amino acids, one each from the light (VL) and heavy (VH) chains, that both present three hypervariable loops (HVRs) or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones."

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

In certain embodiments, filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-antigen clones is desired, the subject is immunized with antigen to generate an antibody response, and spleen cells and/or circulating B cells other peripheral blood lymphocytes (PBLs) are recovered for library construction. In one embodiment, a human antibody gene fragment library biased in favor of anti-antigen antibody clones is obtained by generating an anti-antigen antibody response in transgenic mice carrying a functional human immunoglobulin gene array (and lacking a functional endogenous antibody production system) such that antigen immunization gives rise to B cells producing human antibodies against antigen. The generation of human antibody-producing transgenic mice is described below.

Additional enrichment for anti-antigen reactive cell populations can be obtained by using a suitable screening procedure to isolate B cells expressing antigen-specific membrane bound antibody, e.g., by cell separation using antigen affinity chromatography or adsorption of cells to fluorochrome-labeled antigen followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which antigen is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci.* (USA), 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci.* (USA), 86: 5728-5732 (1989). To maximize complementarity, degeneracy can be incorporated in the primers as described in Orlandi et al. (1989) or Sastry et al. (1989). In certain embodiments, library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798

(1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al., *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

The antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique* 1: 11-15 (1989)) in the method of Hawkins et al., *J. Mol. Biol.*, 226: 889-896 (1992) or in the method of Gram et al., *Proc. Natl. Acad. Sci USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities of about $10^{-9}$ M or less.

Screening of the libraries can be accomplished by various techniques known in the art. For example, antigen can be used to coat the wells of adsorption plates, expressed on host cells affixed to adsorption plates or used in cell sorting, or conjugated to biotin for capture with streptavidin-coated beads, or used in any other method for panning phage display libraries.

The phage library samples are contacted with immobilized antigen under conditions suitable for binding at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci USA*, 88: 7978-7982 (1991), or by alkali, e.g. as described in Marks et al., *J. Mol. Biol.*, 222: 581-597 (1991), or by antigen competition, e.g. in a procedure similar to the antigen competition method of Clackson et al., *Nature*, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for antigen. However, random mutation of a selected antibody (e.g. as performed in some affinity maturation techniques) is likely to give rise to many mutants, most binding to antigen, and a few with higher affinity. With limiting antigen, rare high affinity phage could be competed out. To retain all higher affinity mutants, phages can be incubated with excess biotinylated antigen, but with the biotinylated antigen at a concentration of lower molarity than the target molar affinity constant for antigen. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-antigen clones may be selected based on activity. In certain embodiments, the invention provides anti-antigen antibodies that bind to living cells that naturally express antigen or bind to free floating antigen or antigen attached to other cellular structures. Fv clones corresponding to such anti-antigen antibodies can be selected by (1) isolating anti-antigen clones from a phage library as described above, and optionally amplifying the isolated population of phage clones by growing up the population in a suitable bacterial host; (2) selecting antigen and a second protein against which blocking and non-blocking activity, respectively, is desired; (3) adsorbing the anti-antigen phage clones to immobilized antigen; (4) using an excess of the second protein to elute any undesired clones that recognize antigen-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding hybridoma-derived monoclonal antibodies or phage display Fv clones is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130: 151 (1992).

DNA encoding the Fv clones can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. An Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In certain embodiments, an Fv clone derived from human variable DNA is fused to human constant region DNA to form coding sequence(s) for full- or partial-length human heavy and/or light chains.

DNA encoding anti-antigen antibody derived from a hybridoma can also be modified, for example, by substituting the coding sequence for human heavy- and light-chain constant domains in place of homologous murine sequences derived from the hybridoma clone (e.g. as in the method of Morrison et al., *Proc. Natl. Acad. Sci. USA*, 81: 6851-6855 (1984)). DNA encoding a hybridoma- or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies.

(iv) Humanized and Human Antibodies

Various methods for humanizing non-human antibodies are known in the art. For example, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.*, 151:2296 (1993); Chothia et al., *J. Mol. Biol.*, 196:901 (1987)). Another method uses a particular framework derived from the consensus sequence of all human antibodies of a particular subgroup of light or heavy chains. The same framework may be used for several different humanized antibodies (Carter et al., *Proc. Nall. Acad Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to one embodiment of the method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human antibodies in the formulations and compositions described herein can be constructed by combining Fv clone variable domain sequence(s) selected from human-derived phage display libraries with known human constant domain sequence(s) as described above. Alternatively, human monoclonal antibodies can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al, *Proc. Natl. Acad. Sci. USA*, 90:2551 (1993); Jakobovits et al., *Nature*, 362:255-258 (1993); Bruggermann et al., *Year in Immuno.*, 7:33 (1993); and Duchosal et al. *Nature* 355:258 (1992).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science*, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering*, ed. Borrebaeck, supra. The antibody fragment may also be a "linear antibody", e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci.* *USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Antibodies with more than two valencies are contemplated. For example, trispecific antibodies can be prepared. Tuft et al. *J. Immunol.* 147: 60 (1991).

(vii) Single-Domain Antibodies

In some embodiments, an antibody is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

(viii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(ix) Antibody Derivatives

The antibodies in the formulations and compositions of the invention can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

(x) Vectors, Host Cells, and Recombinant Methods

Antibodies may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(a) Signal Sequence Component

An antibody in the formulations and compositions described herein may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(b) Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter.

(c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics,* 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology,* 8:135 (1990). Stable multi-copy expression vectors for secretion of mature recombinant human serum albumin by industrial strains of *Kluyveromyces* have also been disclosed. Fleer et al., *Bio/Technology,* 9:968-975 (1991).

(d) Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(e) Enhancer Element Component

Transcription of a DNA encoding an antibody by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody-encoding sequence, but is preferably located at a site 5' from the promoter.

(f) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

(g) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, Methods in Molecular Biology, Vol. 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the invention, particularly for transfection of *Spodoptera frugiperda* cells.

Plant cell cultures of cotton, corn, potato, soybean, petunia, tomato, duckweed (Leninaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

(h) Culturing the Host Cells

The host cells used to produce an antibody may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(xi) Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

B. Selecting Biologically Active Antibodies

Antibodies produced as described above may be subjected to one or more "biological activity" assays to select an antibody with beneficial properties from a therapeutic perspective. The antibody may be screened for its ability to bind the antigen against which it was raised. For example, for an anti-DR5 antibody (e.g., drozitumab), the antigen binding properties of the antibody can be evaluated in an assay that detects the ability to bind to a death receptor 5 (DR5).

In another embodiment, the affinity of the antibody may be determined by saturation binding; ELISA; and/or competition assays (e.g. RIA's), for example.

Also, the antibody may be subjected to other biological activity assays, e.g., in order to evaluate its effectiveness as a therapeutic. Such assays are known in the art and depend on the target antigen and intended use for the antibody.

To screen for antibodies which bind to a particular epitope on the antigen of interest, a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

C. Preparation of the Formulations

Provided herein are methods of preparing a formulation comprising a protein and a compound which prevents oxidation of the protein in the formulation. The formulation may be prepared by mixing the protein having the desired degree of purity with a compound which prevents oxidation of the protein in the formulation (such as a liquid formulation). In certain embodiments, the protein to be formulated has not been subjected to prior lyophilization and the formulation of interest herein is an aqueous formulation. In some embodiments, the protein is a therapeutic protein. In certain embodiments, the protein is an antibody. In further embodiments, the antibody is a polyclonal antibody, a monoclonal antibody, a humanized antibody, a human antibody, a chimeric antibody, or antibody fragment. In certain embodiments, the antibody is a full length antibody. In one embodiment, the antibody in the formulation is an antibody fragment, such as an F(ab')$_2$, in which case problems that may not occur for the full length antibody (such as clipping of the antibody to Fab) may need to be addressed. The therapeutically effective amount of protein present in the formulation is determined by taking into account the desired dose volumes and mode(s) of administration, for example. From about 1 mg/mL to about 250 mg/mL, from about 10 mg/mL to about 250 mg/mL, from about 15 mg/mL to about 225 mg/mL, from about 20 mg/mL to about 200 mg/mL, from about 25 mg/mL to about 175 mg/mL, from about 25 mg/mL to about 150 mg/mL, from about 25 mg/mL to about 100 mg/mL, from about 30 mg/mL to about 100 mg/mL or from about 45 mg/mL to about 55 mg/mL is an exemplary protein concentration in the formulation. In some embodiments, the protein described herein is susceptible to oxidation. In some embodiments, one or more of the amino acids selected from the group consisting of methionine, cysteine, histidine, tryptophan, and tyrosine in the protein is susceptible to oxidation. In some embodiments, tryptophan in the protein is susceptible to oxidation. In some embodiments, methionine in the protein is susceptible to oxidation. In some embodiments, an antibody provided herein is susceptible to oxidation in the Fab portion and/or the Fc portion of the antibody. In some embodiments, an antibody provided herein is susceptible to oxidation at a tryptophan amino acid in the Fab portion of the antibody. In a further embodiment, the tryptophan amino acid susceptible to oxidation is in a CDR of the antibody. In some embodiments, an antibody provided herein is susceptible to oxidation at a methionine amino acid in the Fc portion of the antibody.

The formulations provided herein comprise a protein and a compound which prevents oxidation of the protein in the formulation, wherein the compound is of formula:

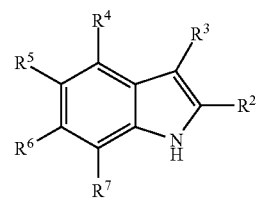

wherein $R^2$ is selected from hydrogen, hydroxyl, —COOH, and —CH$_2$COOH;

$R^3$ is selected from hydrogen, hydroxyl, —COOH, —CH$_2$COOH, and —CH$_2$CHR$^{3a}$(NH$_2$); wherein $R^{3a}$ is COOH or hydrogen; $R^4$, $R^5$, $R^6$, and $R^7$ are independently selected from hydrogen and hydroxyl; provided that one of $R^2$, $R^3$, $R^4$, $R^5$, $R^6$, and $R^7$ is hydroxyl; or a pharmaceutically acceptable salt thereof.

In some embodiments, the compound is a compound of formula:

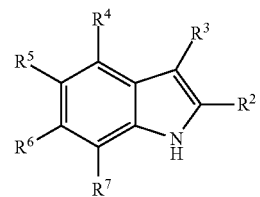

wherein $R^2$ and $R^3$ are independently selected from hydrogen, hydroxyl, —COOH, and —CH$_2$COOH; and $R^4$, $R^5$, $R^6$, and $R^7$ are independently selected from hydrogen and hydroxyl; provided that one of $R^2$, $R^3$, $R^4$, $R^5$, $R^6$, and $R^7$ is hydroxyl; or a pharmaceutically acceptable salt thereof.

In some embodiments, the compound is a compound of formula:

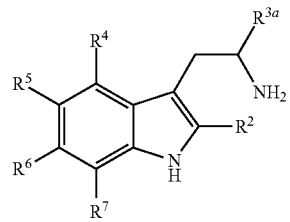

wherein $R^{3a}$ is COOH or hydrogen; $R^2$, $R^4$, $R^5$, $R^6$, and $R^7$ are independently selected from hydrogen and hydroxyl, provided that one of $R^2$, $R^4$, $R^5$, $R^6$, and $R^7$ is hydroxyl; or a pharmaceutically acceptable salt thereof.

In some embodiments, $R^4$, $R^5$ or $R^7$ in any of the formula above is hydroxyl. In a further embodiment, the compound is selected from the group consisting of 5-hydroxy-tryptophan, 5-hydroxy indole, 7-hydroxy indole, and serotonin. In a further embodiment, the compound is selected from the group consisting of 4-hydroxy indole, 5-hydroxy indole-3-acetic acid, and 7-hydroxy indole-2-carboxylic acid. In some embodiments, the formulation is a liquid formulation. In some embodiments, the compound in the formulation is at a concentration from about 0.3 mM to about 10 mM, or up to the highest concentration that the compound is soluble in the formulation. In certain embodiments, the compound in the formulation is at a concentration from about 0.3 mM to about 9 mM, from about 0.3 mM to about 8 mM, from about 0.3 mM to about 7 mM, from about 0.3 mM to about 6 mM, from about 0.3 mM to about 5 mM, from about 0.3 mM to about 4 mM, from about 0.3 mM to about 3 mM, from about 0.3 mM to about 2 mM, from about 0.5 mM to about 2 mM, from about 0.6 mM to about 1.5 mM, or from about 0.8 mM to about 1.25 mM. In some embodiments, the compound in the formulation is about 1 mM. In some embodiments, the compound prevents oxidation of one or more amino acids in the protein. In some embodiments, the compound prevents oxidation of one or more amino acids in the protein selected from group consisting of tryptophan, methionine, tyrosine, histidine, and/or cysteine. In some embodiments, the compound prevents oxidation of the protein by a reactive oxygen species (ROS). In a further embodiment, the reactive oxygen species is selected from the group consisting of a singlet oxygen, a superoxide ($O_2$—), an alkoxyl radical, a peroxyl radical, a hydrogen peroxide ($H_2O_2$), a dihydrogen trioxide ($H_2O_3$), a hydrotrioxy radical ($HO_3$.), ozone ($O_3$), a hydroxyl radical, and an alkyl peroxide. In a further embodiment, the compound prevents oxidation of one or more amino acids in the Fab portion of an antibody. In another further embodiment, the compound prevents oxidation of one or more amino acids in the Fc portion of an antibody.

In some embodiments, the formulation (such as a liquid formulation) further comprises one or more excipients selected from the group consisting of a stabilizer, a buffer, a surfactant, and a tonicity agent. In some embodiments, the formulation is prepared in a pH-buffered solution. The buffer of this invention has a pH in the range from about 4.5 to about 7.0. In certain embodiments the pH is in the range from pH 4.5 to 6.5, in the range from pH 4.5 to 6.0, in the range from pH 4.5 to 5.5, in the range from pH 4.5 to 5.0, in the range from pH 5.0 to 7.0, in the range from pH 5.5 to 7.0, in the range from pH 5.7 to 6.8, in the range from pH 5.8 to 6.5, in the range from pH 5.9 to 6.5, in the range from pH 6.0 to 6.5, or in the range from pH 6.2 to 6.5. In certain embodiments of the invention, the formulation has a pH of 6.2 or about 6.2. In certain embodiments of the invention, the formulation has a pH of 6.0 or about 6.0. Examples of buffers that will control the pH within this range include organic and inorganic acids and salts thereof. For example, acetate (e.g., histidine acetate, arginine acetate, sodium acetate), succinate (e.g., histidine succinate, arginine succinate, sodium succinate), gluconate, phosphate, fumarate, oxalate, lactate, citrate, and combinations thereof. The buffer concentration can be from about 1 mM to about 600 mM, depending, for example, on the buffer and the desired isotonicity of the formulation. In certain embodiments, the formulation comprises a histidine buffer (e.g., in the concentration front about 5 mM to 100 mM). Examples of histidine buffers include histidine chloride, histidine acetate, histidine phosphate, histidine sulfate, histidine succinate, etc. In certain embodiments, the formulation comprises histidine and arginine (e.g., histidine chloride-arginine chloride, histidine acetate-arginine acetate, histidine phosphate-arginine phosphate, histidine sulfate-arginine sulfate, histidine succinate-arginine succinate, etc.). In certain embodiments, the formulation comprises histidine in the concentration from about 5 mM to 100 mM and the arginine is in the concentration of 50 mM to 500 mM. In one embodiment, the formulation comprises histidine acetate (e.g., about 20 mM)-arginine acetate (e.g., about 150 mM). In certain embodiments, the formulation comprises histidine succinate (e.g., about 20 mM)-arginine succinate (e.g., about 150 mM). In certain embodiments, histidine in the formulation from about 10 mM to about, 35 mM, about 10 mM to about 30 mM, about 10 mM to about 25 mM, about 10 mM to about 20 mM, about 10 mM to about 15 mM, about 15 mM to about 35 mM, about 20 mM to about 35 mM, about 20 mM to about 30 mM or about 20 mM to about 25 mM. In further embodiments, the arginine in the formulation is from about 50 mM to about 500 mM (e.g., about 100 mM, about 150 mM, or about 200 mM).

The formulation (such as a liquid formulation) of the invention can further comprise a saccharide, such as a disaccharide (e.g., trehalose or sucrose). A "saccharide" as used herein includes the general composition $(CH_2O)n$ and derivatives thereof, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, iso-maltulose, etc.

A surfactant can optionally be added to the formulation (such as a liquid formulation). Exemplary surfactants include nonionic surfactants such as polysorbates (e.g. polysorbates 20, 80, etc.) or poloxamers (e.g. poloxamer 188, etc.). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, from about 0.005% to about 0.2%, from about 0.01% to about 0.1%, or from about 0.02% to about 0.06%, or about 0.03% to about 0.05%. In certain embodiments, the surfactant is present in the formulation in an amount of 0.04% or about 0.04%. In certain embodiments, the surfactant is present in the formulation in an amount of 0.02% or about 0.02%. In one embodiment, the formulation does not comprise a surfactant.

In one embodiment, the formulation contains the above-identified agents (e.g., antibody, buffer, saccharide, and/or surfactant) and is essentially free of one or more preservatives, such as benzyl alcohol, phenol, m-cresol, chlorobutanol and benzethonium Cl. In another embodiment, a preservative may be included in the formulation, particularly where the formulation is a multidose formulation. The concentration of preservative may be in the range from about 0.1% to about 2%, preferably from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Exemplary pharmaceutically acceptable excipients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The formulation may further comprise metal ion chelators. Metal ion chelators are well known by those of skill in the art and include, but are not necessarily limited to aminopolycarboxylates, EDTA (ethylenediaminetetraacetic acid), EGTA (ethylene glycol-bis(beta-aminoethyl ether)-N, N,N',N'-tetraacetic acid), NTA (nitrilotriacetic acid), EDDS (ethylene diamine disuccinate), PDTA (1,3-propylenediaminetetraacetic acid), DTPA (diethylenetriaminepentaacetic acid), ADA (beta-alaninediacetic acid), MGCA (methylglycinediacetic acid), etc. Additionally, some embodiments herein comprise phosphonates/phosphonic acid chelators.

Tonicity agents are present to adjust or maintain the tonicity of liquid in a composition. When used with large, charged biomolecules such as proteins and antibodies, they may also serve as "stabilizers" because they can interact with the charged groups of the amino acid side chains, thereby lessening the potential for inter- and intra-molecular interactions. Tonicity agents can be present in any amount between 0.1% to 25% by weight, or more preferably between 1% to 5% by weight, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

The formulation herein may also contain more than one protein or a small molecule drug as necessary for the particular indication being treated, preferably those with complementary activities that do not adversely affect the other protein. For example, where the antibody is anti-DR5 (e.g., drozitumab), it may be combined with another agent (e.g., a chemotherapeutic agent, and anti-neoplastic agent).

In some embodiments, the formulation is for in vivo administration. In some embodiments, the formulation is sterile. The formulation may be rendered sterile by filtration through sterile filtration membranes. The therapeutic formulations herein generally are placed into a container having a sterile access port, for example, an intravenous solution bag or vial having a stopper pierceable by a hypodermic injection needle. The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation of the invention may be stored in liquid or non-liquid formulation (e.g., lyophilized). The lyophilized formulation may be reconstituted before administration. In some embodiments, the concentrations of proteins, compounds and other excipients described herein refer to concentrations in reconstituted formulations. In some embodiments, the formulation is stable upon storage. In some embodiments, the protein in the liquid formulation is stable upon storage at about 0 to 5° C. for at least about 12 months, at least about 18 months, at least about 21 months, or at least about 24 months (or at least about 52 weeks). In some embodiments, the physical stability, chemical stability, or biological activity of the protein in the formulation is evaluated or measured. Any methods known the art may be used to evaluate the stability and biological activity. In some embodiments, the stability is measured by oxidation of the protein in the formulation (such as a liquid formulation) after storage. Stability can be tested by evaluating physical stability, chemical stability, and/or biological activity of the antibody in the formulation around the time of formulation as well as following storage. Physical and/or stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may result in aggregation, deamidation (e.g. Asn deamidation), oxidation (e.g. Trp oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation differences, etc. In some embodiments, the oxidation in a protein is determined using one or more of RP-HPLC, LC/MS, or tryptic peptide mapping. In some embodiments, the oxidation in an antibody is determined as a percentage using one or more of RP-HPLC, LC/MS, or tryptic peptide mapping and the formula of:

$$\% \text{ Fab Oxidation} = 100 \times \frac{\text{Oxidized Fab Peak Area}}{\text{Fab Peak Area} + \text{Oxidized Fab Peak Area}}$$

$$\% \text{ Fc Oxidation} = 100 \times \frac{\text{Oxidized Fc Peak Area}}{\text{Fc Peak Area} + \text{Oxidized Fc Peak Area}}$$

The formulations to be used for in vivo administration should be sterile. This is readily accomplished by filtration through sterile filtration membranes, prior to, or following, preparation of the formulation.

Also provided herein are methods of making a protein formulation or preventing oxidation of a protein in a protein formulation comprising adding an amount of a compound that prevents oxidation of a protein to the protein formulation, wherein the compound is of formula:

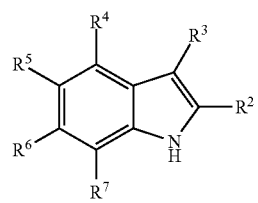

wherein $R^2$ is selected from hydrogen, hydroxyl, —COOH, and —CH$_2$COOH;

$R^3$ is selected from hydrogen, hydroxyl, —COOH, —CH$_2$COOH, and —CH$_2$CHR$^{3a}$(NH$_2$); wherein $R^{3a}$ is COOH or hydrogen; $R^4$, $R^5$, $R^6$, and $R^7$ are independently selected from hydrogen and hydroxyl; provided that one of $R^2$, $R^3$, $R^4$, $R^5$, $R^6$, and $R^7$ is hydroxyl; or a pharmaceutically acceptable salt thereof.

In some embodiments, the compound is a compound of formula:

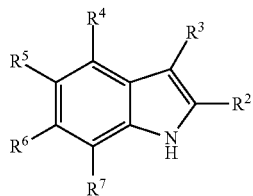

wherein $R^2$ and $R^3$ are independently selected from hydrogen, hydroxyl, —COOH, and —CH$_2$COOH; and $R^4$, $R^5$, $R^6$, and $R^7$ are independently selected from hydrogen and hydroxyl; provided that one of $R^2$, $R^3$, $R^4$, $R^5$, $R^6$, and $R^7$ is hydroxyl; or a pharmaceutically acceptable salt thereof.

In some embodiments, the compound is a compound of formula:

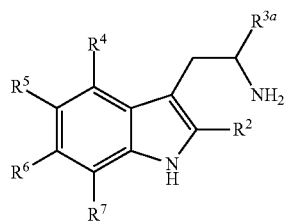

wherein $R^{3a}$ is COOH or hydrogen; $R^2$, $R^4$, $R^5$, $R^6$, and $R^7$ are independently selected from hydrogen and hydroxyl, provided that one of $R^2$, $R^4$, $R^5$, $R^6$, and $R^7$ is hydroxyl; or a pharmaceutically acceptable salt thereof.

In some embodiments, $R^4$, $R^5$ or $R^7$ is hydroxyl. In some embodiments, the compound is selected from the group consisting of 5-hydroxy-tryptophan, 5-hydroxy indole, 7-hydroxy indole, and serotonin. In certain embodiments, the formulation comprises an antibody. The amount of the compound that prevents oxidation of the protein as provided herein is from about 0.3 mM to about 10 mM or any of the amounts disclosed herein.

III. Administration of Protein Formulations

The formulation (such as a liquid formulation) is administered to a mammal in need of treatment with the protein (e.g., an antibody), preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. In one embodiment, the liquid formulation is administered to the mammal by intravenous administration. For such purposes, the formulation may be injected using a syringe or via an IV line, for example. In one embodiment, the liquid formulation is administered to the mammal by subcutaneous administration.

The appropriate dosage ("therapeutically effective amount") of the protein will depend, for example, on the condition to be treated, the severity and course of the condition, whether the protein is administered for preventive or therapeutic purposes, previous therapy, the patient's clinical history and response to the protein, the type of protein used, and the discretion of the attending physician. The protein is suitably administered to the patient at one time or over a series of treatments and may be administered to the patient at any time from diagnosis onwards. The protein may be administered as the sole treatment or in conjunction with other drugs or therapies useful in treating the condition in question. As used herein the term "treatment" refers to both therapeutic treatment and prophylactic or preventative measures. Those in need of treatment include those already with the disorder as well as those in which the disorder is to be prevented. As used herein a "disorder" is any condition that would benefit from treatment including, but not limited to, chronic and acute disorders or diseases including those pathological conditions which predispose the mammal to the disorder in question.

In a pharmacological sense, in the context of the invention, a "therapeutically effective amount" of a protein (e.g., an antibody) refers to an amount effective in the prevention or treatment of a disorder for the treatment of which the antibody is effective. As a general proposition, the therapeutically effective amount of the protein administered will be in the range of about 0.1 to about 50 mg/kg of patient body weight whether by one or more administrations, with the typical range of protein used being about 0.3 to about 20 mg/kg, preferably about 0.3 to about 15 mg/kg, administered daily, for example. However, other dosage regimens may be useful. For example, a protein can be administered at a dose of about 100 or 400 mg every 1, 2, 3, or 4 weeks or is administered a dose of about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 15.0, or 20.0 mg/kg every 1, 2, 3, or 4 weeks. The dose may be administered as a single dose or as multiple doses (e.g., 2 or 3 doses), such as infusions. The progress of this therapy is easily monitored by conventional techniques.

IV. Methods of Screening for Compounds for the Prevention of Protein Oxidation Also provided herein are methods of screening a compound that prevents oxidation of a protein in a protein composition. In some embodiments, the method comprises selecting a compound that has lower oxidation potential and less photosensitivity as compared to L-tryptophan, and testing the effect of the selected compound on preventing oxidation of the protein. In some embodiments, the photosensitivity is measured based on the amount of H$_2$O$_2$ produced by the compound upon light exposure. For example, a liquid composition comprising the compound can be exposed to 250 W/m$^2$ light for a certain amount of time and the resulting H$_2$O$_2$ formation is quantified. A compound with less photosensitivity produces less H$_2$O$_2$ upon exposure to a certain amount of light than a compound that has a higher photosensitivity upon exposure to the same amount of light. In some embodiments, the compound that produces less than about 10%, less than about 15%, less than about 20%, less than about 25% of the amount of H$_2$O$_2$ is selected. H$_2$O$_2$ can be produced by oxidation of amino acid residues in a protein that are susceptible to oxidation. In some embodiments, the oxidation potential is measured by cyclic voltammetry.

In some embodiments, the selected compound is tested for the effect on preventing oxidation of the protein by reactive oxygen species generated by 2,2'-azobis(2-amidinopropane) dihydrochloride (AAPH), light, and/or a Fenton reagent. In any of the embodiments herein, a method described in the Examples may be used for screening a compound that prevents oxidation of a protein in a protein composition.

V. Articles of Manufacture

In another embodiment of the invention, an article of manufacture is provided comprising a container which holds the formulation of the invention and optionally provides instructions for its use. Suitable containers include, for example, bottles, vials and syringes. The container may be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: The Antioxidant L-Trp Produces ROS that Oxidize Monoclonal Antibodies in Protein Formulations Monoclonal antibodies have been shown to produce ROS through the antibody catalyzed water oxidation pathway (ACWOP) wherein antibodies potentially catalyze a reaction between water and singlet oxygen generating hydrogen peroxide (Wentworth et al., *Science* 293(5536):1806-11 (2001); Wentworth et al., *Proc Natl Acad Sci USA* 97(20): 10930-5 (2000)). In the ACWOP, a variety of ROS, including superoxide anion, dihydrogen trioxide, ozone, and even hydrotrioxy radical are generated in the pathway toward production of hydrogen peroxide (Zhu et al., *Proc Natl Acad Sci USA* 101(8):2247-52 (2004)). It has been shown that surface exposed tryptophans in a monoclonal anti-DR5 antibody, drozitumab (CAS number 912628-39-8), also referred to herein as mAb1, act as substrate ($^1O_2$ and $O_2^-$) generators that facilitate ACWOP even under mild light conditions in a time and concentration dependent manner (Sreedhara et al., *Mol. Pharmaceutics* (2013)). It was demonstrated that mAb1 was particularly susceptible to oxidation during storage under pharmaceutically relevant conditions (Sreedhara et al., *Mol. Pharmaceutics* (2013)). Oxidation was shown to be site specific and localized to Trp53 (W53) on the heavy chain CDR (Fab) as evaluated by tryptic peptide mapping. Additionally, a reverse-phase HPLC assay was used to measure the total oxidation in the HC Fab and Fc regions of mAb1 via a papain digestion, DTT reduction, and reverse-phase separation. Peaks from RP-HPLC were identified using LC/MS and showed a strong correlation with results of the tryptic peptide map, indicating that the RP method could be used as a surrogate for detection of W53 (i.e. % Fab) oxidation. In the RP papain digest method, Fab and Fc oxidation peaks eluted before their respective main peaks, allowing the quantification of % Fab and % Fc oxidation in relation to their total peak areas. The study further showed that hydrogen peroxide could serve as a surrogate for a number of ROS, including superoxide and singlet oxygen.

To determine if limited light exposure can be used as an accelerated stress model to study protein oxidation, the same human monoclonal IgG1 antibody (mAb1) was used to screen and evaluate potential antioxidants. L-tryptophan (L-Trp), an antioxidant used in protein formulations, has been recently shown to be photosensitive (Igarashi et al., *Anal Sci* 23(8):943-8 (2007)) and to have the ability to produce $H_2O_2$ upon light exposure. The sensitivity of mAb1 to L-Trp under light stress was evaluated, with and without the addition of L-methionine (L-Met) as a potential antioxidant. mAb1 was expressed in Chinese Hamster Ovary (CHO) cells and purified by a series of chromatography methods including affinity purification by protein A chromatography and ion-exchange chromatography. mAb1 was prepared at 5 mg/mL in a formulation of 20 mM histidine acetate, 250 mM trehalose and 0.02% polysorbate 20 in a glass vial and with 1 mM L-Trp and various concentrations of L-Met, ranging from 10 mM to 100 mM, and exposed to eight hours of light at 250 W/m$^2$ in an Atlas SunTest CPS+ Xenon Test Instrument (Chicago, Ill.). Control vials were wrapped in aluminum foil and treated similarly. After light exposure, solutions were prepared for analysis by reverse-phase HPLC. For RP-HPLC, mAb1 solution from the stress study was prepared to 1.1 mg/mL in 0.1 M Tris, 4.4 mM EDTA, and 1.1 mM cysteine. 150 µL of 0.1 mg/mL papain was added to 1.35 mL of the mAb1 solution before incubation at 37° C. for two hours. Following incubation, 900 µL of the solution was combined with 100 µL of 1 M dithiothreitol (DTT) and incubated for another thirty minutes at 37° C. Samples were then run on an Agilent, Inc. 1100/1200 HPLC system (Santa Clara, Calif.) equipped with UV detection at 280 nm in conjunction with a Varian, Inc. Pursuit 3 µm, 2 mm ID×250 mm diphenyl column (Palo Alto, Calif.). Mobile Phase A was 0.1% TFA in water. Mobile Phase B was 0.1% TFA in acetonitrile. The mobile phase gradient increased linearly from 34% B at 0 minutes to 43% B at 50.0 minutes, then to 95% B at 50.1 minutes. The gradient remained at 95% B until 60.1 minutes, and then decreased linearly from 95% B to 34% B between 60.1 and 60.2 minutes. The gradient remained at 34% B until the end of the cycle at 80.2 minutes. The column temperature was 65° C., total flow rate was 0.2 mL/min, and injection volume of each sample was 6 µL. Chromatograms were then integrated for quantification of oxidation.

Analysis of the light exposure effects of L-Trp and L-Met on mAb1 Fab oxidation showed that the mAb1 reference material (no light exposure) and the foil control had about 2% Fab oxidation (FIG. 1A). Since the foil control and the reference material showed the same level of Fab oxidation, it was unlikely that heat alone is causing oxidation of the Fab. When mAb1 was exposed to light ("No Excipient" sample), the Fab oxidation doubled to 4%. With the addition of 1 mM L-Trp, the Fab oxidation increased to almost 9%, suggesting that free L-Trp was generating ROS under light exposure that may have resulted in oxidation of W53 on the Fab. Further addition of 10, 25, 50, and 100 mM L-Met to formulation containing 1 mM L-Trp appeared to reduce Fab oxidation slightly, but even 100 molar excess of L-Met dis not reduce Fab oxidation to the level of the foil control (FIG. 1A).

Oxidation in the Fc region of mAb1 has been shown to be predominately of Met residues Met 254 and Met 430 (Sreedhara et al., *Mol. Pharmaceutics* (2013)). Analysis of the light exposure effects of L-Trp and L-Met on mAb1 Fc oxidation showed that the mAb1 reference material and foil control had about 8% Fc oxidation even before exposure to light (FIG. 1B). Exposure to light resulted in only a minor increase in Fc oxidation ("No Excipient") for mAb1 in formulation buffer. However, incubation with 1 mM L-Trp resulted in over 20% oxidation at these Met sites in the Fc region as seen by the RP-HPLC assay. Addition of various concentrations of L-Met (10, 25, 50 and 100 mM) to formulations containing 1 mM L-Trp reduced the amount of Fc oxidation, although even 100 mM L-Met dis not reduce Fc oxidation to the level of the controls (FIG. 1B).

Figure 2:
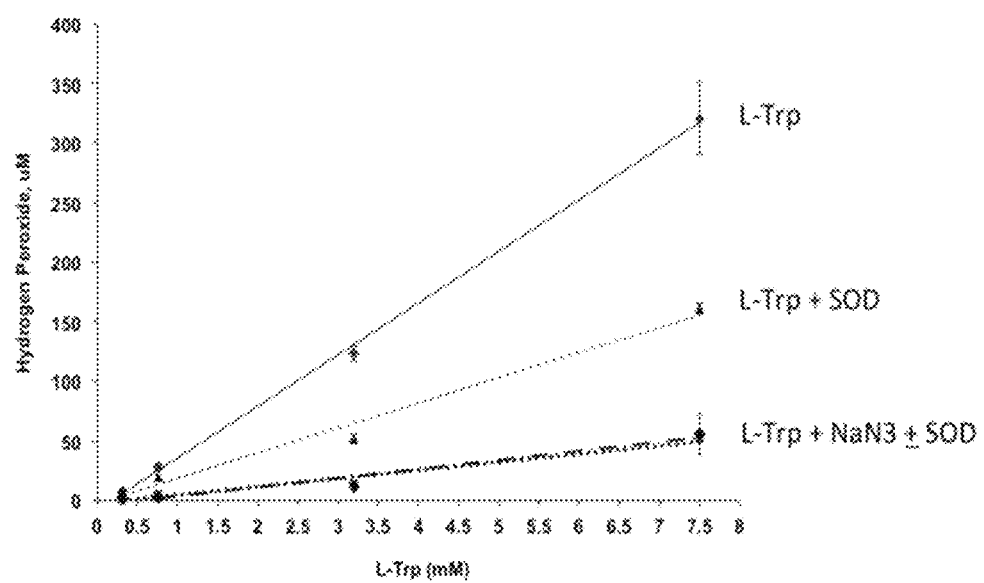
FIG. 2 is a graph showing dose dependent H$_2$O$_2$ production by L-Trp. Diamonds indicate L-Trp alone; Triangles indicate L-Trp+SOD; Circles and Squares indicate L-Trp+NaN$_3$±SOD. All studies were performed in 20 mM L-His HCl, pH 5.5.

It was previously reported that L-Trp produced $H_2O_2$ via superoxide ion and in a sub-stoichiometric fashion while antibodies under similar conditions were producing catalytic amounts (Wentworth et al., *Science* 293(5536):1806-11 (2001); McCormick et al., *Journal of the American Chemical Society* 100:312-313 (1978)). To test the susceptibility of free L-Trp under pharmaceutically relevant conditions, such as under both ICH and ambient light conditions, formulations comprising 0.32 mM to 7.5 mM of L-Trp were exposed for 3 hours at 250 W/m² UV light and about 150 k lux visible light. Samples were taken and analyzed immediately via the Amplex assay to detect the amount of $H_2O_2$ generated under these conditions. A large quantity of $H_2O_2$ was generated by free L-Trp upon light exposure in a concentration dependent manner (FIG. 2). This $H_2O_2$ generation was reduced greatly in the presence of 50 mM sodium azide, a known quencher of singlet oxygen (FIG. 2). When L-Trp was incubated with a combination of 50 mM $NaN_3$ and 150 U superoxide dismutase (SOD) or SOD alone, significant amounts of $H_2O_2$ were still detected in the samples not containing $NaN_3$. This indicated that, in addition to singlet oxygen, superoxide ion was also generated upon photo-irradiation that was converted to $H_2O_2$ by SOD.

Figure 3:
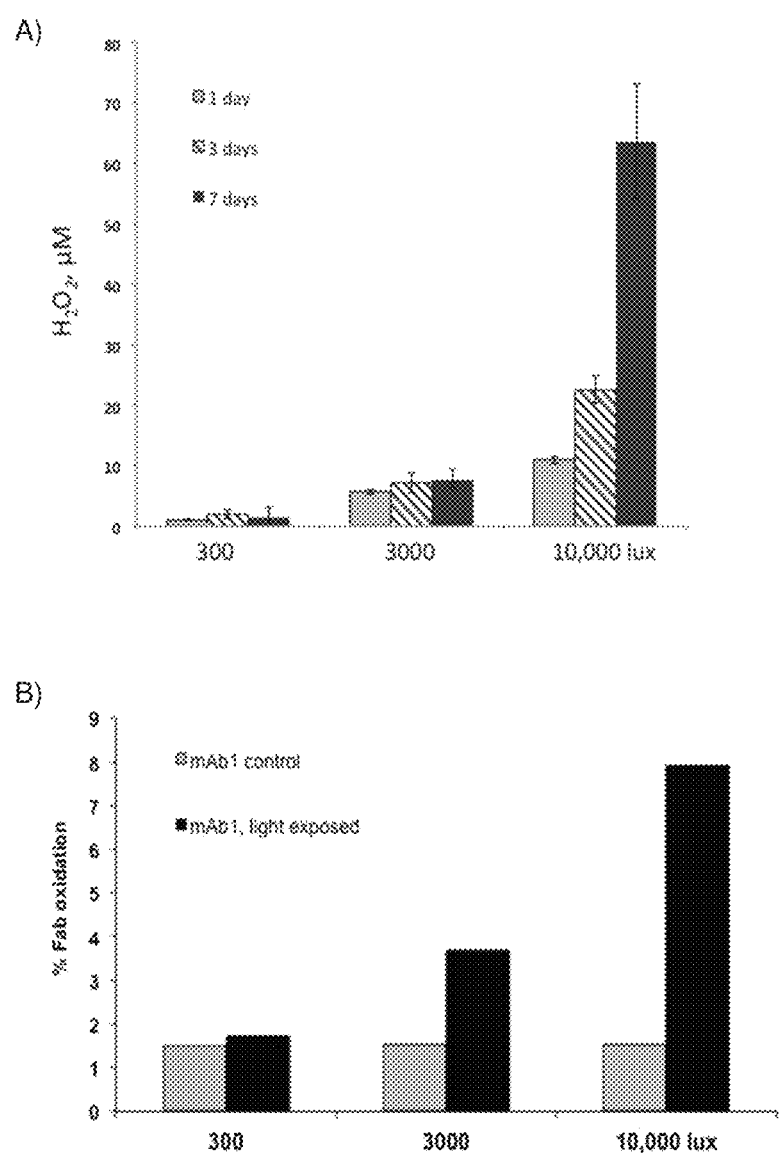
FIG. 3 is a series of graphs demonstrating A) Hydrogen peroxide ($H_2O_2$) production in 50 mg/mL mAb1 formulations containing 3.2 mM L-Trp when exposed to ambient light conditions for 1, 3 and 7 days and B) Percent (%) Fab oxidation in mAb1 formulations containing 3.2 mM L-Trp after 10 days of exposure to ambient light conditions.

While confirming the photosensitivity of free L-Trp under ICH light conditions, the effect of ambient light that was typically seen in laboratories was studied. Measurements using a DLM1 digital light meter in various labs indicated an average of 300 lux on a lab benchtop (with white fluorescent lighting), an average of 3000 lux in a laminar flow hood (with white fluorescent lighting) and about 10000 lux for a windowsill exposed to southeast sunlight. Under these conditions, L-Trp in formulation buffers containing 50 mg/mL mAb1 produced hydrogen peroxide in the micromolar range as detected using the Amplex assay (FIG. 3A). Peroxide production increased with both luminosity (300, 3000, and 10000 lux) and time (1, 3, and 7 days). The protein samples were further analyzed using the mAb1 specific RP-HPLC assay and showed increased heavy chain Fab oxidation corresponding to oxidation in W53 with increased luminosity (FIG. 3B). At the same time, % Fc oxidation in mAb1 under these conditions increased from 5 to 40% between 300 and 10000 lux, respectively. These levels of light exposure and time were determined to be pharmaceutically relevant for drug substance handling under ambient light and temperature before fill/finish operations and potentially while inspecting drug product vials. These results supported that L-Trp is photosensitive and that it produces several reactive oxygen species, including singlet oxygen, superoxide and $H_2O_2$ that can be detrimental to mAb product quality and that care should be taken while handling and storing L-Trp containing buffers.

Example 2: Screening of Candidate Antioxidant Compounds

Tryptophan (Trp) is an electron rich amino acid that undergoes oxidative and electrophilic addition reactions in the presence of ROS such as hydroxyl radicals and singlet oxygen. Any potential antioxidant to protect Trp oxidation in proteins should have similar if not superior reactivity towards these ROS. A series of compounds that were either based on the L-Trp structure or have been reported to have antioxidant properties were evaluated. Compounds screened for antioxidant ability in this study included derivatives of tryptophan, indole, aromatic acids such as salicylic acid and anthranilic acid, and some vitamins. The chemical structures of the various compounds used were based on (A) Tryptophan derivatives (B) Kynurenine (C) Indole derivatives and (D) Aromatic acid derivatives:

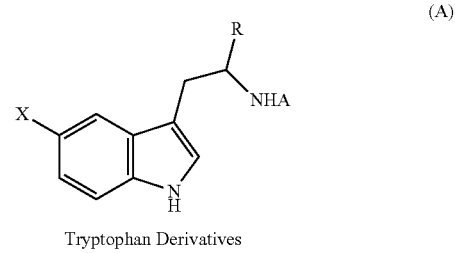

Tryptophan Derivatives (A)

| Name | R | X | A |
| --- | --- | --- | --- |
| L-Tryptophan | COOH | H | H |
| 5-Hydroxy-Tryptophan | COOH | OH | H |
| 5-Methoxy-Tryptophan | COOH | $OCH_3$ | H |
| 5-Amino-Tryptophan | COOH | $NH_2$ | H |
| 5-Fluoro-Tryptophan | COOH | F | H |
| N-Acetyl-Tryptophan | COOH | H | $CH_3C(O)$ |
| Tryptamine | H | H | H |
| Tryptophanamide | $CONH_2$ | H | H |
| Serotonin | H | OH | H |
| Melatonin | H | $OCH_3$ | $CH_3C(O)$ |

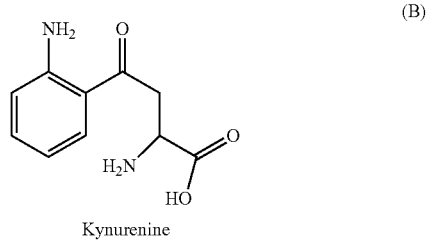

Kynurenine (B)

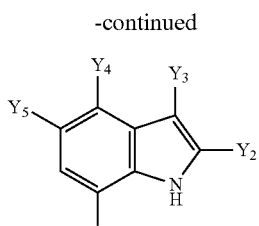

Indole Derivatives

| Name | $Y_2$ | $Y_3$ | $Y_4$ | $Y_5$ | $Y_7$ |
|---|---|---|---|---|---|
| Indole | H | H | H | H | H |
| Indole-3-Acetic Acid | H | CH$_2$COOH | H | H | H |
| 4-Hydroxy Indole | H | H | OH | H | H |
| 5-Hydroxy Indole | H | H | H | OH | H |
| 5-Hydroxy Indole-3-Acetic Acid | H | CH$_2$COOH | H | OH | H |
| 7-Hydroxy Indole | H | H | H | H | OH |
| 7-Hydroxy Indole-2-Carboxylic Acid | COOH | H | H | H | OH |

Aromatic Acid Derivatives

| Name | $Z_1$ | $Z_2$ |
|---|---|---|
| Salicylic Acid | OH | H |
| 5-Hydroxy Salicylic Acid | OH | OH |
| Anthranilic Acid | NH$_2$ | H |
| 5-Hydroxy Anthranilic Acid | NH$_2$ | OH |

Candidate Antioxidant Compounds Obtained from a Photosensitivity Screening Assay.

While L-Trp may have been an effective antioxidant under certain circumstances, its photosensitivity may limit its utility during normal processing without special precautions. Hence the photosensitivity of the above molecules was investigated and rated for their $H_2O_2$ generation capability with respect to L-Trp. As a screening tool, antioxidant candidates were exposed to light for four hours at 250 W/m$^2$ and the resulting $H_2O_2$ formation was quantified by the Amplexassay. Specifically, antioxidants were prepared to 1 mM in 20 mM histidine acetate buffer at pH 5.5. The 1 mM antioxidant solutions were aliquoted into glass vials (2 mL/glass vial) and exposed to four hours of light at 250 W/m$^2$ in an Atlas SunTest CPS+ Xenon Test Instrument (Chicago, Ill.). Total UV dose was 90 watt-hours/square meter and total visible dose was 0.22 million lux hours over the 4-hour period. Control vials were wrapped in aluminum foil and treated similarly. The amount of hydrogen peroxide generated after exposure to light was measured using the Amplex® Ultra Red Assay (Invitrogen, Carlsbad, Calif.) following the manufacturer's recommended procedure. On addition of horseradish peroxidase (HRP), the dye reacted 1:1 stoichiometrically with $H_2O_2$, resulting in the production of fluorescent oxidation product resorufin. In this study, fluorescence readings were obtained using a Spectra Max M2 Micro-plate Reader (Molecular Devices, Sunnyvale, Calif.) with excitation and emission set at 560 nm and 590 nm, respectively. Final $H_2O_2$ concentrations were determined using a standard curve ranging from 0 μm to 20 μm.

Figure 4:
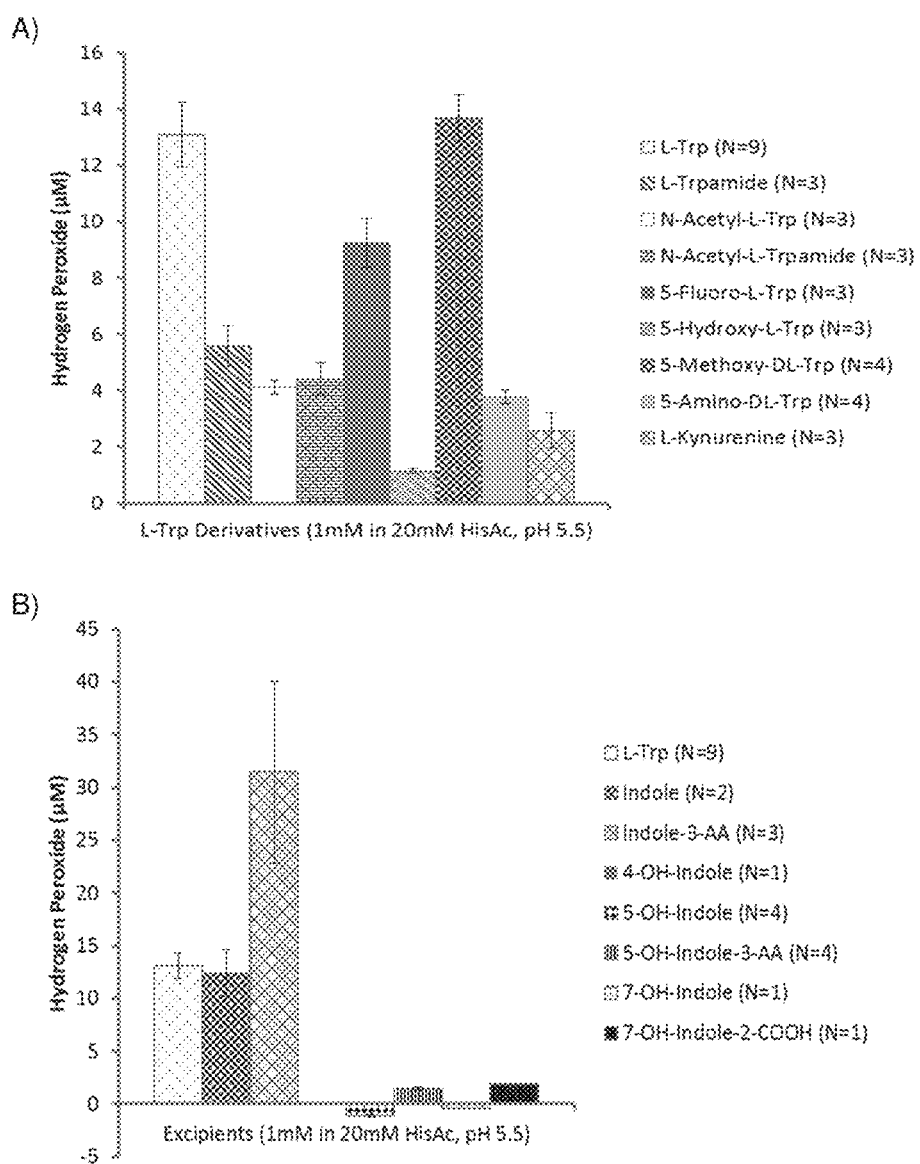
FIG. 4 is a series of graphs showing hydrogen peroxide generation by tryptophan derivatives and indole derivatives under light stress for 4 hours at 250 W/m². A) Screening of tryptophan derivatives (1 mM) for hydrogen peroxide (µM) generation in a 20 mM HisAc pH5.5 formulation. B) Screening of indole derivatives (1 mM) for hydrogen peroxide (µM) generation in a 20 mM HisAc pH5.5 formulation.

Analysis of hydrogen peroxide ($H_2O_2$) generation by tryptophan derivatives upon light exposure showed that under similar conditions of light (corresponding to 0.22 million lux hours over a 4-hour period) and buffer (20 mM L-His-acetate, pH 5.5), 5-hydroxy-L-tryptophan produced about one tenth of the $H_2O_2$, while kynurenine produced about one fifth of the $H_2O_2$, when compared to L-Trp (FIG. 4A). Other tryptophan derivatives produced anywhere between 30% and 105% of the $H_2O_2$ produced by L-Trp. In comparison to L-Trp, Trolox (a water soluble Vitamin E derivative) produced 123 times more $H_2O_2$, and pyridoxine (Vitamin B6) produced 5 times more $H_2O_2$ (Table 1). Indole, which has a basic structure like L-Trp, behaved similarly to L-Trp, but indole-3-acetic acid produced twice as much $H_2O_2$ (FIG. 4B). The hydroxy derivatives of indole behaved like 5-OH-L-tryptophan in that they produced negligible amounts of $H_2O_2$ upon light exposure. Several biochemically relevant derivatives of L-Trp, namely tryptamine, serotonin and melatonin were also tested. Tryptamine produced about half as much $H_2O_2$ as L-Trp (FIG. 4A). Interestingly, serotonin (5-hydroxytryptamine) behaved much like the 5-OH derivatives of indole and tryptophan, producing very little $H_2O_2$ upon light exposure, while melatonin (N-acetyl-5-methoxytryptamine) produced less than a third of the $H_2O_2$ produced by L-Trp (Table 1).

TABLE 1

Hydrogen Peroxide Production Ratio between Tested Compounds and L-Trp

| Compound | ($H_2O_2$ produced by Compound)/($H_2O_2$ produced by L-Trp) |
|---|---|
| L-Trp | 1 |
| L-Trpamide | 0.43 |
| N-Acetyl-L-Trp | 0.31 |
| N-Acetyl-L-Trpamide | 0.34 |
| 5-Fluoro-L-Trp | 0.71 |
| 5-Hydroxy-L-Trp | 0.09 |
| 5-Methoxy-DL-Trp | 1.05 |
| 5-Amino-DL-Trp | 0.29 |
| L-Kynurenine | 0.20 |
| Trolox | 122.75 |
| Pyridoxine | 5.16 |
| Indole | 0.95 |
| Indole-3-Acetic Acid | 2.40 |
| 4-Hydroxyindole | 0.00 |
| 5-Hydroxyindole | −0.08 |
| 5-Hydroxyindole-3-Acetic Acid | 0.11 |
| 7-Hydroxyindole | −0.03 |
| 7-Hydroxyindole-2-Carboxylic Acid | 0.15 |
| Tryptamine | 0.53 |
| Serotonin (5-Hydroxytryptamine) | 0.03 |
| Melatonin (N-Acetyl-5-Methoxytryptamine) | 0.28 |
| Salicylic Acid | 0.03 |
| 5-Hydroxysalicylic Acid | 0.84 |
| Anthranilic Acid | 2.50 |
| 5-Hydroxyanthranilic Acid | 0.44 |

Figure 5:
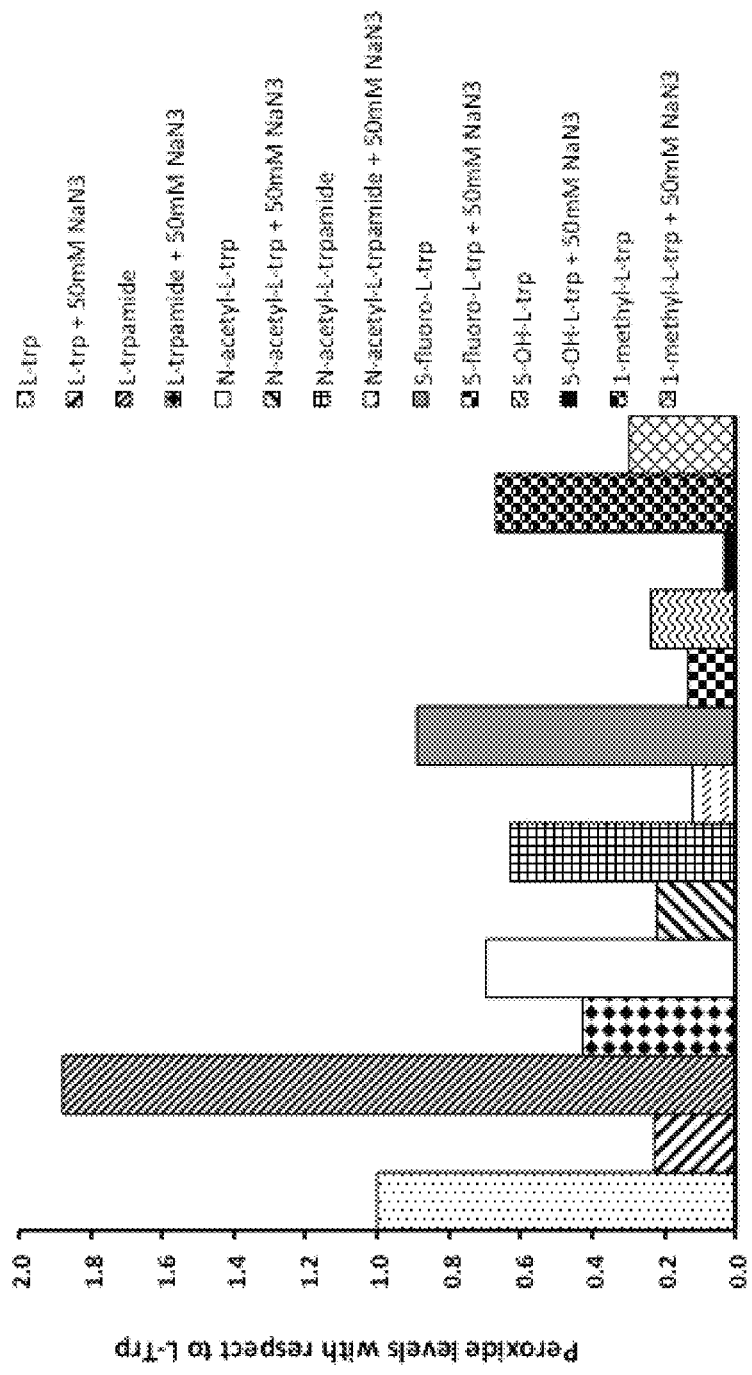
FIG. 5 is a graph showing the effect of $NaN_3$ on $H_2O_2$ production by various Trp derivatives upon light exposure. Data is shown as a ratio with respect to peroxide generated by L-Trp.

In order to understand the ROS formed during photo-irradiation, several of the Trp derivatives in the presence of 50 mM NaN$_3$, a known singlet oxygen quencher, were tested under light exposure as described above. All the compounds tested showed a substantial decrease in the amount of hydrogen peroxide generated under these conditions, indicating that singlet oxygen was a major ROS created upon photo-irradiation of Trp and its derivatives (FIG. 5).

Other aromatic compounds such as salicylic acid and derivatives were also tested based on their reported antioxidant properties (Baltazar et al., Curr Med Chem 18(21): 3252-64 (2011)). Salicylic acid produced very little $H_2O_2$ upon light exposure while its 5-OH derivative behaved like L-Trp (Table 1). On the other hand, anthranilic acid produced twice as much $H_2O_2$ as L-Trp but 5-OH-anthranilic acid produced half as much $H_2O_2$ compared to L-Trp (Table 1).

Candidate Antioxidant Compounds Obtained from a CV Screening Assay.

Based on the results from the photosensitivity screening assay, compounds with aromatic ring substitutions appeared to impact the amount of hydrogen peroxide generated. Since the goal was preferential oxidation of the excipient rather than the protein drug, excipients that had low oxidation potentials may have served as effective antioxidants. The oxidation/reduction characteristics of the compounds were investigated. Several compounds, including L-Trp and derivatives, were evaluated for the protection of Trp oxidation in proteins using cyclic voltammetry (CV) and rank ordered based on their oxidation potentials (Table 2). Specifically, the candidate antioxidants were dissolved in deionized water and then added to a 0.2 M lithium perchlorate electrolyte solution. Solutions were characterized with an EG&G Princeton Applied Research Model 264A Polarograph/Voltammeter with a Model 616 RDE Glassy Carbon Electrode as working electrode. Solutions were scanned from −0.10 V to +1.50 V at a scan rate of either 100 or 500 mV/sec. The analytical cell was purged for four minutes with nitrogen before scanning of each antioxidant solution. The input was a linear scan of the potential of a working electrode, and the output was measurement of the resulting current. As the potential was scanned (linearly increased or decreased), electrochemically active species in the CV cell underwent oxidation and reduction reactions at the surface of the working electrode that resulted in a current which was continuously measured. Redox reactions were characterized by sharp increases or decreases in current (peaks). The potential at which an oxidation reaction occurred was referred to as the anodic peak potential (or oxidation potential), and the potential at which a reduction occurred was referred to as is the cathodic peak (or reduction) potential.

The oxidation potentials of the excipients in this study ranged from 0.410 to 1.080 V vs Ag/AgCl (Table 2). Under these conditions, L-Trp had an irreversible oxidation potential of 0.938 V vs Ag/AgCl. Nine compounds were found to have a lower oxidation potential than L-Trp, including all of the 5-OH compounds which had oxidation potentials between 0.535 and 0.600 V vs Ag/AgCl. Of all the compounds tested, 5-amino-DL-tryptophan had the lowest oxidation potential at 0.410 V, while the N-acetyl compounds (0.730-0.880 V), and 5-methoxy-DL-tryptophan (0.890 V) were also below L-Trp. Seven compounds had higher oxidation potential than L-Trp (Table 2). These were indole-3-acetic acid, 5-fluoro-L-tryptophan, tryptamine, L-tryptophanamide, L-kynurenine, 5-nitro-DL-tryptophan, and salicylic acid. Salicylic acid had the highest oxidation potential in this study (1.080 V vs Ag/AgCl). All the tested compounds showed non-reversible CV indicating that once oxidized, the species did not tend to receive electrons and probably could not be involved in further electrochemical reactions.

TABLE 2

Oxidation Potentials of Excipients

| Compound | Oxidation Potential (V vs Ag/AgCl) |
|---|---|
| 5-amino-DL-tryptophan | 0.410 |
| 5-hydroxyindole-3-acetic acid | 0.535 |
| 5-hydroxy-L-tryptophan | 0.565 |
| 5-hydroxyindole | 0.580 |
| Serotonin HCl (5-hydroxytryptamine HCl) | 0.600 |
| Melatonin (N-acetyl-5-methoxytryptamine) | 0.730 |
| N-acetyl-L-tryptophan | 0.875 |
| N-acetyl-L-tryptophanamide | 0.880 |
| 5-methoxy-DL-tryptophan | 0.890 |
| L-tryptophan | 0.938 |
| Indole-3-acetic acid | 0.948 |
| 5-fluoro-L-tryptophan | 0.965 |
| Tryptamine HCl | 1.010 |
| L-tryptophanamide | 1.015 |
| L-kynurenine | 1.040 |
| 5-nitro-DL-tryptophan | 1.055 |
| Salicylic acid | 1.080 |

Oxidation (anodic peak) potentials were measured using cyclic voltammetry with a glassy carbon working electrode in 0.2M lithium perchlorate.

Figure 6:
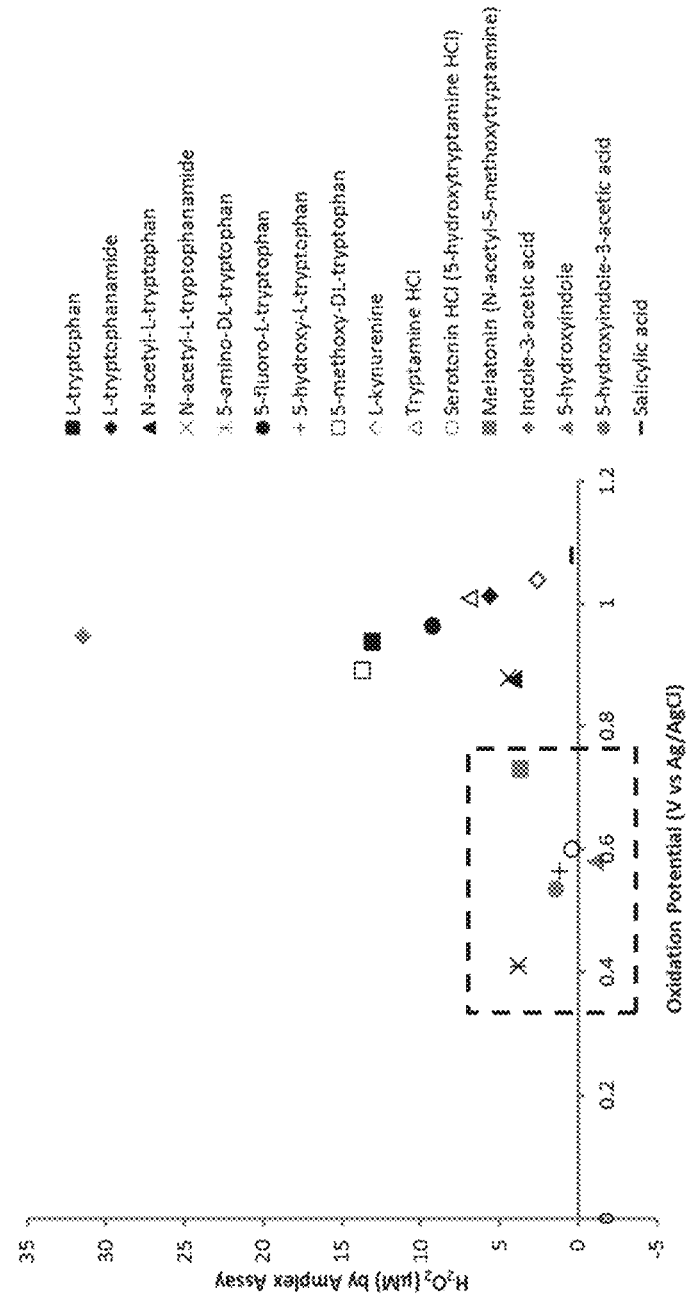
FIG. 6 is a graph showing the correlation between oxidation potential and light-induced peroxide formation. The boxed region shows candidate antioxidant compounds.

A correlation was determined between oxidation potential and light-induced $H_2O_2$ generation for 16 compounds that had oxidation potentials above and below the oxidation potential of L-Trp, and $H_2O_2$ production levels above and below that of L-Trp (FIG. 6). Since indole and tryptophan behaved similarly in $H_2O_2$ production under light exposure, it was possible that substitutions on the $C_3$ position of the 5 membered ring did not affect this property. However, tryptamine with a —$CH_2CH_2NH_2$ substitution and indole-3-acetic acid with a —$CH_2COOH$ substitution at the $C_3$ position produced two times less and two times more $H_2O_2$, respectively, than L-Trp. These data indicated that the $C_3$ substitutions played a role in photo-activation and peroxide generation. The $C_3$ substitutions did not affect the oxidation potentials of the molecules, whereas indole per se had significantly lower oxidation potential than L-Trp under these experimental conditions. Substitutions at the $C_5$ of the 6-membered aromatic ring behaved quite predictably. In general, compounds with electron donating groups such as —$NH_2$ and —OH had lower oxidation potentials than their parent compounds and also showed low levels of $H_2O_2$ production upon photo-activation (e.g. 5-amino-DL-tryptophan, 5-hydroxyindole-3-acetic acid, 5-hydroxy-L-tryptophan, 5-hydroxyindole, serotonin). Similarly, compounds with high oxidation potential produced more $H_2O_2$ (5-methoxy-DL-tryptophan, L-Trp, indole-3-acetic acid, 5-fluoro-L-tryptophan) under these conditions. There were exceptions to this correlation; some compounds had high oxidation potential but did not produce much $H_2O_2$ (e.g. salicylic acid and L-kynurenine) indicating that there were potentially other mechanisms that played an important role for these six membered aromatic compounds that may not have been observed with compounds containing the indole backbone of L-Trp. The area of interest was the quadrant which contained compounds with lower oxidation potential and lower $H_2O_2$ production upon light exposure than L-Trp (FIG. 6, dashed box). Compounds with these two qualities were considered as new candidate antioxidants because they could (1) oxidize faster than Trp on the protein and (2) produce very little $H_2O_2$ during long term storage and/or ambient processing during drug product production and therefore could protect the protein from further oxidation under these conditions.

Example 3: Candidate Antioxidant Compounds Reduced Oxidation of Monoclonal Antibody Formulations Compounds that, compared to L-Trp, produced less $H_2O_2$ upon light treatment as well as those with lower oxidation potentials than L-Trp were chosen for evaluation of for their possible antioxidant properties using AAPH, light, and Fenton reaction as oxidative stress models (Table 3). mAb1 was used as a model protein to evaluate the effectiveness of select candidate antioxidants to protect against Trp oxidation by the different oxidation stress models. Each stress model produced oxidation through a different mechanism and therefore each was valuable in the assessment of biopharmaceutical stability. AAPH, or 2,2'-Azobis(2-Amidinopropane) Dihydrochloride, is used as a stress model to mimic alkyl peroxides potentially generated from formulation excipients such as degraded polysorbate. Decomposition of AAPH generates alkyl, alkoxyl, and alkyl peroxyl radicals that have been shown to oxidize amino acid residues in proteins, including methionine, tyrosine, and tryptophan residues (Ji et al., *J Pharm Sci* 98(12):4485-500 (2009); Chao et al., *Proc Natl Acad Sci USA* 94(7):2969-74 (1997)). Similarly, controlled light could be used as a stress model to mimic ambient light exposure that drugs may experience during processing and storage. Light-induced oxidation of biopharmaceuticals was shown to proceed through a singlet oxygen ($^1O_2$) and/or superoxide anion ($O_2^-$) mechanism (Sreedhara et al., *Mol. Pharmaceutics* (2013)). The Fenton reaction is also commonly used as an oxidative stress model. This mixture of $H_2O_2$ and Fe ions generates oxidation through a metal catalyzed, hydroxyl radical mechanism (Prousek et al., *Pure and Applied Chemistry* 79(12):2325-2338 (2007)), and is used to model metal residue from stainless steel surfaces used in drug manufacturing and storage.

TABLE 3

Oxidation Stress Models

| Stress Model | Mechanism | Purpose |
|---|---|---|
| AAPH | Alkyl peroxides, alkyl radical catalyzed | Mimic alkyl peroxides from degraded polysorbate |
| Light | Singlet oxygen ($^1O_2$), superoxide anion ($O_2^-$), $H_2O_2$ | Mimic ambient light exposure during processing and storage |
| Fenton ($H_2O_2$ + Fe) | Hydroxyl radical, metal catalyzed | Mimic metal residue from stainless steel surfaces |

Tryptophan (W53) oxidation on mAb1 was thoroughly characterized previously using a RP-HPLC and LC-MS method (Sreedhara et al., *Mol. Pharmaceutics* (2013)). Briefly, mAb1 was digested with papain to generate Heavy Chain (HC) Fab, HC Fc, and Light Chain fragments. The fragments were reduced with DTT, and then separated and identified via Liquid Chromatography-Mass Spectrometry (LC-MS). Oxidized versions of the HC Fab and HC Fc were found to elute earlier than their native counterparts. Comparison of area integrated under the oxidized and native peaks was used to quantify HC Fab and Fc oxidation. In addition, LC-MS/MS peptide maps (by trypsin digestion and by Lys-C digestion) showed that oxidation of the HC Fab was primarily of a Trp residue, W53, while oxidation of the HC Fc was attributed predominantly to oxidation of two Met residues, M254 and M430. By using the papain digest RP-HPLC method in the present study it was possible to investigate Trp residue oxidation by quantifying HC Fab oxidation, and Met residue oxidation by quantifying HC Fc oxidation.

% Fab oxidation and % Fc oxidation were calculated as follows:

$$\% \text{ Fab Oxidation} = 100 \times \frac{\text{Oxidized } Fab \text{ Peak Area}}{Fab \text{ Peak Area} + \text{Oxidized } Fab \text{ Peak Area}}$$

$$\% \text{ Fc Oxidation} = 100 \times \frac{\text{Oxidized } Fc \text{ Peak Area}}{Fc \text{ Peak Area} + \text{Oxidized } Fc \text{ Peak Area}}$$

For the mAb1 stress study, mAb1 was prepared to 5 mg/mL in a formulation of 20 mM histidine acetate, 250 mM trehalose, and 0.02% Polysorbate 20. Antioxidants were added at 1 mM. Glass vials containing these formulations were exposed to 250 W/m² light in an Atlas SunTest CPS+ Xenon Test Instrument (Chicago, Ill.). Control vials were wrapped in aluminum foil and treated similarly. After light exposure, solutions were prepared for analysis by reverse-phase HPLC as described above.

For the mAb1 AAPH stress study, mAb1 was prepared to 4 mg/mL in a formulation of 20 mM histidine acetate, 250 mM trehalose, and 0.02% Polysorbate 20. Antioxidants were added at 1 mM. 200 µL of 10 mM AAPH was added to 2 mL of each mAb1 solution and then incubated at 40° C. for 24 hours. After incubation, each solution was buffer exchanged with formulation buffer (20 mM histidine acetate, 250 mM trehalose, and 0.02% Polysorbate 20) using a PD-10 column so that the final mAb1 concentration was 2.3 mg/mL. After buffer exchange, each solution was prepared for analysis by reverse-phase HPLC as described above.

For the mAb1 Fenton stress study, mAb1 was prepared to 3 mg/mL in a formulation of 20 mM histidine hydrochloride pH 6.0. Antioxidants were added at a final concentration of 1 mM. A final concentration of 0.2 mM $FeCl_3$ and 10 ppm $H_2O_2$ were added to each mAb1 solution and then incubated at 40° C. for 3 hours. After incubation, each reaction was quenched by addition of 100 mM L-Met and then prepared for analysis by reverse-phase HPLC as described above.

Figure 7:
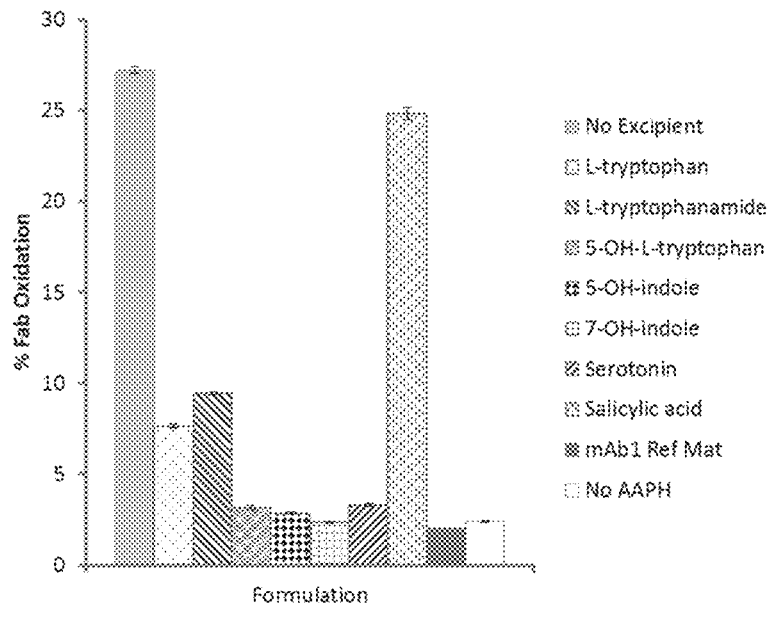
FIG. 7 is a series of graphs showing the oxidation of A) Fab in mAb1, and B) Fc in mAb1 after AAPH incubation. All samples were incubated with AAPH except mAb1 Ref Mat and No AAPH. All samples were incubated at 40° C. except mAb1 Ref Mat. Data shown are the average of three experimental samples ±1SD, except mAb1 Ref Mat which is the average of six HPLC injections without error bars.
Figure 7:
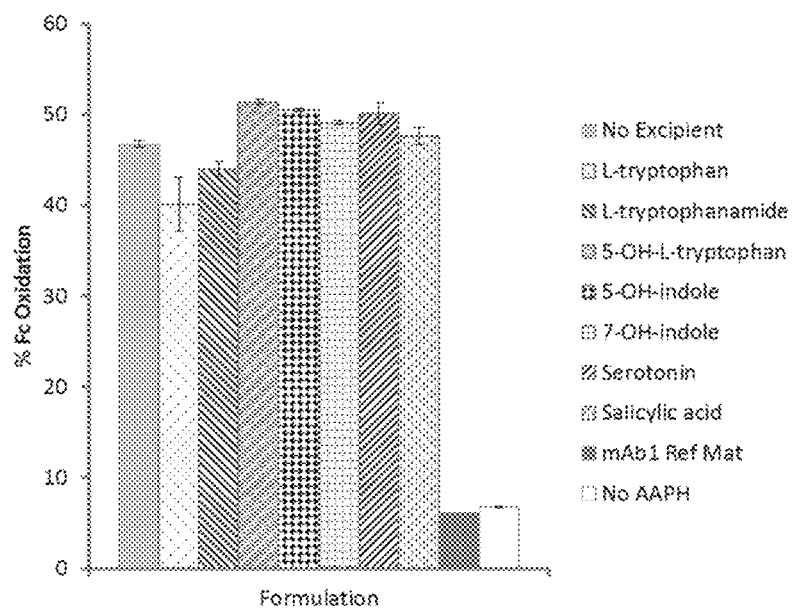

It was determined that incubation of mAb1 with AAPH for 24 hours at 40° C. resulted in 27% Fab (Trp residue) oxidation (FIG. 7A) and 47% Fc (Met residue) oxidation (FIG. 7B). Seven excipients that had been previously screened using light stress and cyclic voltammetry were incubated with mAb1 under the AAPH conditions to evaluate antioxidant capabilities. Six of the seven compounds were found to significantly reduce AAPH-induced Fab oxidation (FIG. 7A). All six of these compounds contained the indole backbone. Moreover, all the hydroxy derivatives tested (5-hydroxy-L-Trp, 5-hydroxyindole, 7-hydroxyindole, and serotonin) reduced Fab oxidation to close to control levels (about 2%). Meanwhile, salicylic acid had almost no effect on Fab oxidation under AAPH stress. None of the excipients appeared to impact the level of AAPH-induced Fc oxidation (FIG. 7B).

Figure 8:
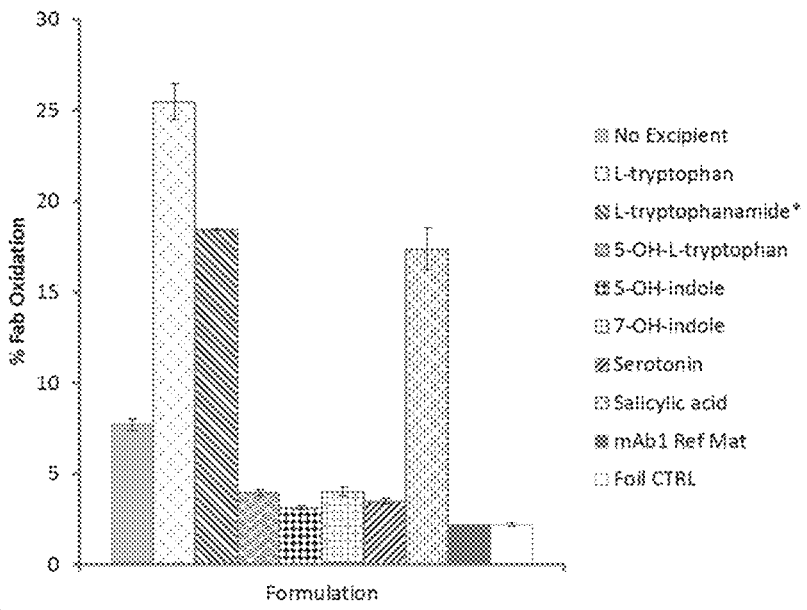
FIG. 8 is series of graphs showing the oxidation of A) Fab in mAb1, and B) Fc in mAb1 after sixteen hours of light exposure at 250 W/m². All vials were placed in the lightbox except the mAb1 Ref Mat. Foil CTRL vials were covered in foil before placement in the lightbox. Three separate experimental vials were averaged for each sample, except L-tryptophanamide (*) was the average of two experimental vials and mAb1 Ref Mat was one vial with three independent injections on the HPLC. Error bars represent one standard deviation.
Figure 8:
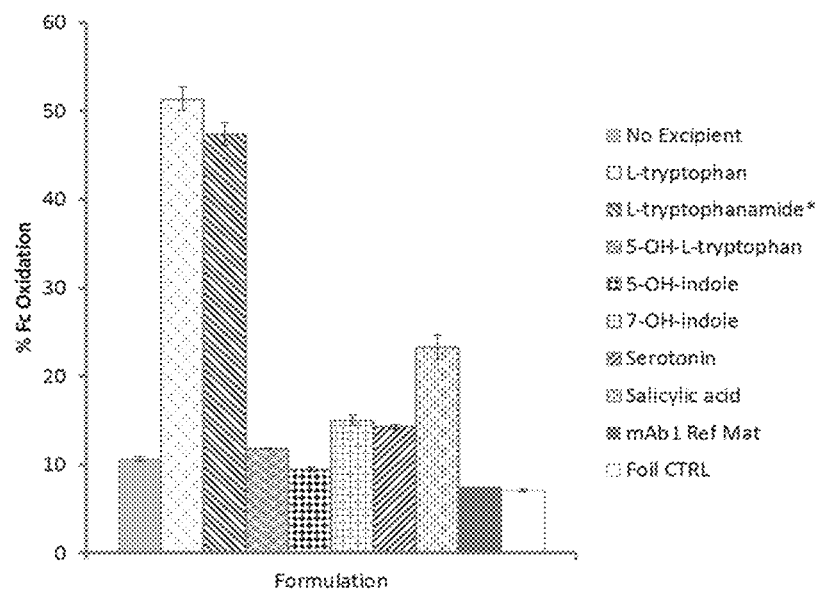

For the light stress study, mAb1 was exposed to 16 hours of light at 250 W/m² while testing the aforementioned seven excipients (FIG. 8). Exposure of mAb1 to light ("No Excipient") increased Fab oxidation 3.5 times over the control level ("mAb1 Ref Mat", FIG. 8A). It was previously shown that L-Trp could protect against Trp oxidation in the model protein Parathyroid Hormone (PTH) (Ji et al., *J Pharm Sci* 98(12):4485-500 (2009)). However, this study found that addition of 1 mM L-Trp to mAb1 increased the Fab oxidation over 11-fold, probably through the production of ROS such as singlet oxygen by light-exposed L-Trp (FIG. 2). Addition of the hydroxy compounds (5-hydroxy-L-Trp, 5-hydroxyindole, 7-hydroxyindole, and serotonin) protected against light-induced Fab oxidation, reducing Fab oxidation to near control levels (FIG. 8A). On the other hand, salicylic acid performed similarly to L-Tryptophanamide, increasing Fab oxidation 8-fold over the control level. Similar results were observed for Fc oxidation under light stress (FIG. 8B). Light exposure of mAb1 resulted in a 40% increase in Fc oxidation over the control level, whereas addition of L-Trp increased Fc oxidation to 7 times the control level. Compared to the control (no excipient), L-Tryptophanamide and salicylic acid also resulted in more Fc oxidation. The hydroxy compounds produced similar Fc oxidation as the no excipient control potentially because they produce much fewer ROS than L-Trp under light exposure. The light screening and $NaN_3$ study results in Example 2 showed a good correlation between the amount of $H_2O_2$ generated by an excipient and Fc Met oxidation of mAb1.

The Fenton reaction, using a mixture of $H_2O_2$ and Fe ions, generates oxidation through a metal catalyzed, hydroxyl radical reaction (Prousek et al., *Pure and Applied Chemistry* 79(12):2325-2338 (2007)). This reaction generated Fab, i.e. tryptophan, oxidation in mAb1. The reaction was also carried out in the presence of select antioxidants that were useful against both AAPH and light induced oxidation as reported above. Data related to the antioxidant properties against Fenton mediated reaction were analyzed using the RP-HPLC assay as described above. The Fenton reaction used 10 ppm of $H_2O_2$ and 0.2 mM of Fe(III). The reaction was incubated at 40° C. for 3 hours, quenched with 100 mM L-Met and analyzed using RP-HPLC after papain digest. All samples were the average of three separate vials, and mAb1 control (Ref Mat) was one vial with five independent injections on the HPLC. Under the conditions tested, the Fenton reaction produced about four times the oxidation in the Fab region of mAb1 over the control. Most of the antioxidants tested, except salicylic acid, showed similar hydroxyl radical quenching properties to L-Trp, which protected the Fab oxidation by about 25% with respect to the no excipient case. In regards to protection against Fc oxidation, the tested excipients (other than salicylic acid) performed slightly better than L-Trp.

What is claimed is:

1. A liquid formulation comprising an antibody and a compound which prevents oxidation of the antibody in the liquid formulation upon storage for at least 8 hours, wherein the compound generates less reactive oxygen species in the formulation compared to tryptophan, wherein the compound is selected from the group consisting of N-acetyl-L-tryptophanamide, 5-amino-DL-tryptophan, and 5-hydroxyindole-3-acetic acid, or a pharmaceutically acceptable salt thereof.

2. The formulation of claim 1 which is a pharmaceutical formulation suitable for administration to a subject.

3. The formulation of claim 1 which is aqueous.

4. The formulation of claim 1, wherein the compound in the formulation is from about 0.3 mM to about 1 mM.

5. The formulation of claim 1, wherein the compound prevents oxidation of tryptophan, cysteine, histidine, tyrosine, and/or methionine in the antibody.

6. The formulation of claim 1, wherein the compound prevents oxidation of the antibody by a reactive oxygen species.

7. The formulation of claim 6, wherein the reactive oxygen species is selected from the group consisting of singlet oxygen, hydrogen peroxide, a hydroxyl radical, and an alkyl peroxide.

8. The formulation of claim 1, wherein the antibody is susceptible to oxidation.

9. The formulation of claim 1, wherein tryptophan in the antibody is susceptible to oxidation.

10. The formulation of claim 1, wherein the antibody is a polyclonal antibody, a monoclonal antibody, a humanized antibody, a human antibody, a chimeric antibody, or antibody fragment.

11. The formulation of claim 1, wherein the antibody concentration in the formulation is about 1 mg/mL to about 250 mg/mL.

12. The formulation of claim 1, which further comprises one or more excipients selected from the group consisting of a stabilizer, a buffer, a surfactant, and a tonicity agent.

13. The formulation of claim 2, wherein the formulation has a pH of about 4.5 to about 7.0.

14. The formulation of claim 1, wherein the formulation has been stored at about 0 to about 5° C. for at least about 12 months.

15. The formulation of claim 14, wherein the formulation has been stored for at least about 18 months.

16. The formulation of claim 14, wherein the formulation has been stored for at least about 24 months.

* * * * *

UNITED STATES PATENT AND TRADEMARK OFFICE
CERTIFICATE OF CORRECTION

PATENT NO. : 11,596,620 B2
APPLICATION NO. : 15/821470
DATED : March 7, 2023
INVENTOR(S) : Sreedhara Alavattam et al.

Page 1 of 1

It is certified that error appears in the above-identified patent and that said Letters Patent is hereby corrected as shown below:

On the Title Page

Item (73) Assignee, change the assignee name from "F. HOFFMANN-LA ROCHE AG, Basel (CN)" to --GENENTECH, INC., South San Francisco, CA (US)--, therefor.

Signed and Sealed this
Nineteenth Day of November, 2024

Katherine Kelly Vidal
*Director of the United States Patent and Trademark Office*